United States Patent
Drozdzal et al.

(10) Patent No.: US 8,611,621 B2
(45) Date of Patent: Dec. 17, 2013

(54) SYSTEM AND METHOD FOR AUTOMATIC DETECTION OF IN VIVO CONTRACTION VIDEO SEQUENCES

(75) Inventors: Michal Drozdzal, Wroclaw (PL); Petia Radeva, Barcelona (ES); Santiago Segui Mesquida, Illes Balears (ES); Laura Igual-Munoz, Barcelona (ES); Carolina Malagelada, Barcelona (ES); Fernando Azpiroz, Barcelona (ES); Jordi Vitria, Barcelona (ES)

(73) Assignee: Given Imaging Ltd., Yoqneam (IL)

( * ) Notice: Subject to any disclaimer, the term of this patent is extended or adjusted under 35 U.S.C. 154(b) by 210 days.

(21) Appl. No.: 13/228,287

(22) Filed: Sep. 8, 2011

(65) Prior Publication Data

US 2012/0057766 A1     Mar. 8, 2012

Related U.S. Application Data

(60) Provisional application No. 61/380,785, filed on Sep. 8, 2010.

(51) Int. Cl.
*G06K 9/00* (2006.01)
*G06K 9/68* (2006.01)

(52) U.S. Cl.
USPC ............ 382/128; 382/217; 382/218; 382/219

(58) Field of Classification Search
USPC ......................................... 382/128, 217–219
See application file for complete search history.

(56) References Cited

U.S. PATENT DOCUMENTS

| | | |
|---|---|---|
| 5,604,531 A | 2/1997 | Iddan et al. |
| 7,009,634 B2 | 3/2006 | Iddan et al. |
| 8,422,755 B2 * | 4/2013 | Drozdzal et al. ............... 382/128 |
| 2009/0202117 A1 | 8/2009 | Vilarino et al. |
| 2009/0284589 A1 | 11/2009 | Radeva et al. |
| 2011/0044515 A1 | 2/2011 | Spyridonos et al. |

OTHER PUBLICATIONS

H. Vu, T Echigo, R. Sagawa et al., "Detection of contractions in adaptive transit time of the small bowel from wireless capsule endoscopy videos," Computers in Biology and Medicine, vol. 39, No. 1, pp. 16-26, 2009.*

U.S. Appl. No. 13/154,544, filed Jun. 7, 2011, Drozdzal et a.

(Continued)

*Primary Examiner* — Utpal Shah

(74) *Attorney, Agent, or Firm* — Pearl Cohen Zedek Latzer Baratz LLP

(57) ABSTRACT

A system and method for comparing captured sequences of in-vivo images with (e.g., template or model) sequences, for example, for computer-automated recognition of contractions. The size of the opening of an in-vivo lumen passageway represented in each frame in a subset of frames of an image stream captured in vivo may be measured. Frames in the subset of frames of the image stream having a local minimum size of the lumen passageway may be identified. The subset of frames may be divided into segments of sequential frames at frames having local maximum lumen sizes before and after the identified frame having a local minimum size of the lumen passageway to generate contraction sequences. A plurality of the contraction sequences may be compared to template sequences. A plurality of the contraction sequences may be displayed.

19 Claims, 11 Drawing Sheets

(56) References Cited

OTHER PUBLICATIONS

Michal Drozdzal, Laura Igual, Jordi Vitria, Carolina Malagelada, Fernando Azpiroz, Petia Radeva, "Aligning Endoluminal Scene Sequences in Wireless Capsule Endoscopy", EEE Computer Society Workshop on Mathematical Methods in Biomedical Image Analysis (MMBIA10), CVPR, pp. 117-124, Jun. 13-18, San Francisco, USA, 2010.

Michal Drozdzal, Petia Radeva, Santi Segui, Fernando Vilariño, Carolina Malagelada, Fernando Azpiroz, Jordi Vitria, " Towards Detection of Measurable Contractions using WCE". Fourth CVC Workshop on the Progress of Research & Development, pp. 1-6, CVCRD, Catalonia, Spain, Oct. 30, 2009.

Fernando Vilariño, Panagiota Spyridonos, Jordi Vitrià and Petia Radeva, "Self Organized Maps for Intestinal Contractions Categorization with Wireless Capsule Video Endoscopy", The 3rd European Medical and Biological Engineering Conference EMBEC'05, IFMBE Proc. Prague, Czech Republic, Nov. 20-25, 2005.

Carolina Malagelada, Fosca De Iorio, Fernando Azpiroz, Anna Accarino, Santi Segui, Petia Radeva and Juan—R. Malagelada, "New Insight Into Intestinal Motor Function via Noninvasive Endoluminal Image Analysis," Gastroenterology, vol. 135, pp. 1155-1162, 2008.

\* cited by examiner

SYSTEM AND METHOD FOR AUTOMATIC DETECTION OF IN VIVO CONTRACTION VIDEO SEQUENCES

REFERENCE TO RELATED APPLICATIONS

This patent application claims priority from U.S. provisional patent application Ser. No. 61/380,785 filed Sep. 8, 2010, which is incorporated herein by reference in its entirety.

FIELD OF EMBODIMENTS OF THE INVENTION

The present invention relates to systems and methods for analyzing an image stream captured in-vivo. More specifically, the present invention relates to systems and methods for automatically detecting a sequence of endoluminal contractions.

BACKGROUND

Peristalsis within a gastro-intestinal (GI) tract transports swallowed food and aids in digestion and eventual evacuation. Peristalsis may result in pressure waves or contractions moving along the GI tract, thereby resulting in motility of a bolus or other object within the GI tract. The bolus may include an in-vivo imaging device able to acquire and transmit images of, for example, the GI tract while the in-vivo imaging device passes through the GI lumen.

Certain pathological conditions may alter the normal motility within the GI tract. Lower than average motility may be caused by, for example, an obstruction, a blockage, or other pathological condition. Motility disorders may be caused by, for example, nervous disorders, and may not necessarily be easily visible. For example, intestinal disorders such as irritable bowel syndrome (IBS) have been linked to irregular contraction rates. For example, faster than average colon contractions rates are common in people with diarrhea-predominant IBS (IBS-D) and slower than average colon contractions rates are common in people with constipation-predominant IBS (IBS-C). Accordingly, a patient's contraction rate may be useful in diagnosing such intestinal disorders.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
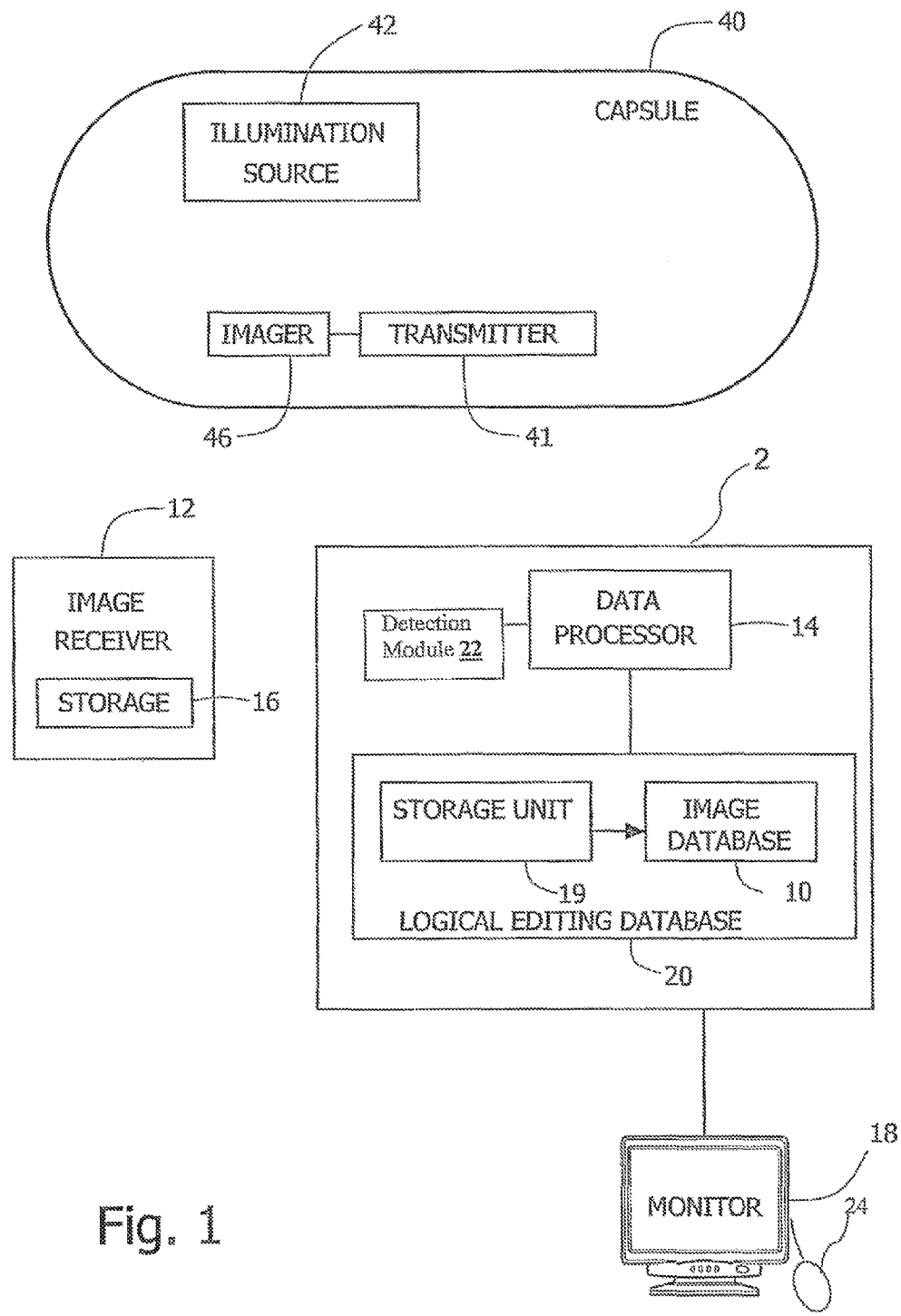
FIG. 1 is a schematic illustration of an in-vivo imaging system, according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

SUMMARY

In an embodiment of the invention, a system and method is provided for comparing captured sequences of in-vivo images with (e.g., template or model) sequences, for example, for computer-automated diagnosis of gastrointestinal events such as contractions, tunnel sequences, static sequences, and wrinkle sequences.

In an embodiment of the invention, a system and method is provided for measuring the size of the opening of an in-vivo lumen passageway represented in each frame in a subset of frames of an image stream captured in vivo. Frames in the subset of frames of the image stream having a local minimum size of the lumen passageway may be identified. The subset of frames may be divided into segments of sequential frames at boundary frames having local maximum lumen sizes before and after the identified frame having a local minimum size of the lumen passageway to generate contraction sequences. A plurality of the contraction sequences may be compared to template sequences. A plurality of the contraction sequences may be displayed.

In an embodiment of the invention, a system and method is provided for receiving a sequence of sizes of the lumen openings represented in each frame in a template image sequence of a contraction. The size of the lumen openings represented in each frame in a captured image stream may be measured. A plurality of frames within the captured image stream for which a local minimum lumen size is measured may be identified. A plurality of captured sequences of different lengths from the captured image stream each captured sequence including a local minimum lumen size frame may be generated. The captured sequence having frames that most closely match the lumen sizes for the template frames may be identified. If the cumulative difference between the lumen sizes for frames in the best fitting captured sequence and the template sequence are within a predetermined threshold range, it may be determined that the captured sequence shows a contraction.

DETAILED DESCRIPTION OF EMBODIMENTS OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a computer or processor readable medium, or a computer or processor storage medium, such as for example a memory, a disk drive, or a USB flash memory, encoding, including or storing instructions, e.g., computer-executable instructions, which when executed by a processor or controller, carry out methods disclosed herein.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

An autonomous in-vivo imaging device may move through the body lumen by peristalsis. Depending on the shape and movement of the endoluminal passageway, the imaging device may move at a variable speed, for example, relatively faster through larger unobstructed passages and relatively slower through narrow or blocked passageways. When the imaging device captures images at a fixed rate (for example, two or four frames per second (fps)), the physical distance between objects being imaged in consecutive frames is also variable, for example, relatively closer when the imaging device moves at a relatively slow speed and relatively farther when the imaging device moves at a relatively fast speed. When the images are combined, in sequence, to form a moving image, the disparity in the proximity of in-vivo objects may generate a skewed or distorted view of the body lumen.

Some mechanisms may compare captured video stream (e.g. moving image stream) segments or scenes with model or template segments or scenes. Each model or template segment may be pre-defined to exhibit, for example, contractions, tunnel sequences, wrinkle sequences (e.g. closed lumen sequences), or other types of endoluminal events or sequences. Models may exhibit or demonstrate other events or in-vivo features. When a match or a relative similarity (e.g. based on a rating or ranking) is found between a captured segment and a template segment, the captured segments may be determined to exhibit a contraction (or another relevant feature or predetermined event). The template segment may be used as a reference bank for automatically detecting, for example, contractions in captured sequences.

Some mechanisms or processes may divide the captured image stream into a plurality of segments of equal length (play-time or frame number), for example, equal to the length of the template segments, for frame comparison. The template segments and captured segments of equal segment length may be compared, for example, using a one-to-one frame comparison. However, contractions in the GI tract often occur for various lengths of time and include various open and closing patterns of the lumen wall. For example, the sequence length of tonic contractions, which may include sustained muscular contraction substantially without intervals of relaxation (e.g., 12-15 seconds of contraction which may be depicted by 25-30 frames at a frame capture rate of 2 fps) may be approximately three times the sequence length of phasic contractions which may include a rhythmic contraction with intervals of relaxation (e.g., 8-10 frames at a frame capture rate of 2 fps). Post-processing operations may alter the sequence length, for example, deleting (e.g., damaged or obstructed) frames from the sequences or adding extra frames (e.g., averaged, merged or combined from adjacent frames) to the sequences. Furthermore, the capsule may capture frames at a variable frame capture rate, further varying the lengths of captured frame contractions. If such variable length captured contractions are compared to the equal length template contraction sequences, some contractions may go undetected.

Furthermore, any disparity in the speed of the imager(s) that captured the image stream segments may cause a further misalignment of anatomical objects and confusion in an automatic, for example, one-to-one, frame comparison. For example, two contraction segments with nearly identical periodicity may be captured at two different imaging device speeds so that the contractions appear to have an out-of-phase periodicity (for example, one sequence shows the opening of a passageway, while the other sequence shows a closing of the passageway). In this example, due to the out-of-phase periodicity of the sequences, a match between these sequences may go undetected.

Accordingly, some embodiments of the invention provide a mechanism for accurately comparing template contraction sequences and captured sequences. Instead of uniformly dividing a captured video stream into sequences of uniform length, according to embodiments of the invention, the division of the captured video stream may be based on the size or shape of the lumen opening or passageway (e.g., the opening or closing of the passageway). Contractions often include an alternating open-closed-open pattern of the lumen passageway associated with a locally maximum-minimum-maximum size of the lumen passageway. By tracking the size of the lumen passageway, a processor or process may identify a passage opening (e.g., a relatively large size for the lumen passageway) and closing (e.g., a relatively small size for the lumen passageway, which may be relatively narrowed compared to that shown in other neighboring frames to form a partial or complete closure). Since a lumen passageway is typically open at the beginning and end of a contraction and a lumen is typically (partially or completely) closed at or near the center of a contraction, a processor or process may divide the video stream at the boundaries of each pair of frames having local maximum sized lumen passageways (e.g., open passageways) that surround or are centered by one or more frames having a local minimum sized lumen passageway (e.g., narrowing or closed passageways). Such a partition may generate contraction sequences with an open-closed-open pattern of the lumen passageway. Since the captured video stream is divided based on patterns of lumen sizes characteristic of contractions and contractions occur for a wide variety of durations, this partition may generate contraction sequences having a plurality of different lengths.

Once the contraction sequences are generated, embodiments of the invention may align each captured and template sequence by correlating frames thereof. Frames of the different sequences may be aligned based on the similarity in anatomical features or events between frames, the phase of contraction of each frame, a direction of change of the image objects between consecutive frames in each sequence, and/or an amount of intestinal deformation between consecutive frames in each sequence. In one embodiment, frames may be aligned based on the size of the opening of the lumen wall (e.g., to match frames in corresponding open or closed phases of a contraction). Out-of-phase or misaligned frames in one sequence may be re-aligned to be in-phase with frames in a different sequence. For example, the processor may align frames from both sequences depicting the opening of a passageway and likewise, may align frames from both sequences depicting the closing of a passageway.

Aligning may produce the best match between the captured and template sequences based on their contraction patterns. Aligning may be, for example, altering a correspondence, correlation, or mapping between frames of two sequences, altering the relative index, duration, or time associated with frames of one or each of the sequences and/or identifying frames or portions of one sequence corresponding to frames or portions of the other sequence. Aligning sequences may include changing the rate, time or length of an image sequence or changing the correspondence or mapping between frames in the sequences, for example, by elongating or shortening one or both sequences. Aligning sequences may include defining a link for each frame in one sequence using a pointer, index, flags, metadata, or other indicator to the corresponding one or more frames or the relative position of the one or more frames in the other sequence.

In one embodiment, the captured video may be divided into a plurality of sequences, each of which may be aligned with the same template sequence. Captured sequences of different lengths or phases of contractile activity may have different alignments to the same template sequence. The alignment may be executed for a single template sequence or repeated for each new one of a plurality of template sequences.

In some embodiments, a sequence may be aligned by elongating, e.g., by inserting additional frames into the sequence, increasing the duration or time-slots associated with each frame, or defining an elongated mapping with another sequence. Extra frames inserted into the sequence may be a duplicate of a previous or subsequent frame or an average, merging or combination of adjacent previous and/or subsequent frames. An elongated mapping between sequences may define a correspondence between each of at least one frame in a first sequence to two or more frames in a second sequence. Instead of a one-to-one correspondence between frames of sequences, an elongated mapping may have a "one-to-many" correspondence. In some embodiments, additional frames may be moved to the memory storing the sequence or alternatively, an index may point to the additional frame in a separate memory.

Similarly, in some embodiments, a sequence may be aligned by shortening or compressing, e.g., by deleting or extracting frames from the sequence, averaging, merging or combining two or more frames into one, decreasing the playtime or time-slots associated with each frame, or defining a compressed mapping between the sequences. Frames deleted from the sequence may be for example frames that are most similar to a previous or subsequent frame or frames that are replaced by an average or combination thereof. A compressed mapping between sequences may define a correspondence between each group of two or more frames in a first sequence to a single frame in a second sequence. An elongated mapping may have a "many-to-one" correspondence.

Although sequences may be compressed or elongated for alignment, frames should typically not be rearranged out of order since frames are generally not captured out of order.

Once the sequences are aligned, a process or processor may compare the visual anatomical objects, events or features of the frames of each sequence in a captured image stream with each of one or more model or template sequences. A plurality of template contraction sequences may each be associated with a different pre-defined type of contraction, for example, phasic occlusive contractions, tonic semi-occlusive contractions, etc., or different contraction properties, for example, defining or representing the symmetry or duration of the contractions. The template sequence may be used as a reference for comparison with other sequences for the analysis, for example, of each individual patient's image stream. In one embodiment, template sequence may be pre-stored in computer software (prior to software use) and may be pre-analyzed and associated with pre-generated annotations, for example, for identifying and diagnosing matching captured sequences loaded by a user operating the software. The processor or process may use pattern recognition and/or feature extraction logic to compare properties of the captured sequence with properties of the template sequences. The properties may include, for example, the size of the lumen opening, color patterns, texture patterns, and/or geometric patterns or shapes, within each frame or changes thereof between consecutive frames. In one embodiment, the processor or process may use a scoring system to quantify and analyze the frame similarity features. For comparison, the template sequences may be matched with each captured sequence having the most similar feature values or score(s).

When the difference between the properties of the compared and template sequences is below a predetermined threshold, the processor may indicate a match therebetween and the processor or process may identify the captured sequence as a verified contraction sequence (e.g., having a contraction of the type pre-associated with the matching template contraction sequence). The processor or process may diagnose or associate the captured sequence with the contraction or motility features associated with the matching template sequence. The processor or process may store, display or otherwise present the associated contraction features or content scores to a user.

Contraction data, for example, pre-associated with a template contraction sequence or generated by evaluating the captured sequence may include, the type of contraction (e.g., phasic or tonic; occlusive, non-occlusive, or semi-occlusive), the size or shape of the lumen opening or ranges thereof, the duration (e.g., length of the contraction sequence in time or frame number) and periodicity of the opening and closing of the contractions, whether the contractions are symmetric (when opening and closing take the same or similar times) or asymmetric (when opening and closing take different times), or the relative symmetry/asymmetry of the contraction (the difference in duration or frame number between the closing and the opening of the contraction), the degree, radius, or direction of contractile deformation or occlusion between the present frame and a consecutive frame, the presence, direction or area of "wrinkles," or other color or pattern features or changes, the number of frames for the opening of the contraction (e.g., between the contractions beginning and midpoint—a central or maximum lumen size frame), the number of frames for the closing of the contraction (e.g., between a central frame and the end of the contraction), the number of frames between the beginning and the end of the contraction, and/or other visual or numerical features.

Reference is made to FIG. 1, which schematically illustrates an in-vivo imaging system according to an embodiment of the invention.

According to some embodiments, a system may include a device, for example, an imaging device 40. Imaging device 40 may be a swallowable in-vivo imaging device, but other sorts of devices or suitable implementations may be used. According to one embodiment, imaging device 40 may communicate with an external receiving and display system to provide display of data, control, or other functions. For example, power may be provided by an internal battery or a wireless receiving system. Other embodiments may have other configurations and capabilities.

Imaging device 40 may include an imager 46, for capturing images, an illumination source 42, for illuminating the body lumen, and a transmitter 41, for transmitting image and possibly other information to a receiving device. Transmitter 41 may include receiver capability, for example, to receive control information. An optical system, including, for example, lenses or mirrors, may aid in focusing reflected light onto the imager 46.

An image receiver 12, which may include an antenna or antenna array, an image receiver storage unit 16, a data processor 14, a data processor storage unit 19, and an image monitor 18, for displaying, for example, the images recorded by the imaging device 40, may be located outside the patient's body in one or more locations. The receiver 12 and image receiver storage unit 16 may be small and portable, and may be worn on the patient's body during recording of the images.

According to one embodiment of the invention, data processor 14, data processor storage unit 19 and monitor 18 may be part of a personal computer or workstation 2 which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components (e.g., data processor 14).

Data processor 14 may include any standard data processor, such as a microprocessor, multiprocessor, accelerator board, or any other serial or parallel high performance data processor.

Image monitor 18 may be a computer screen, a conventional video display, or any other device capable of providing image or other data.

Preferably, the imager 46 is a suitable complementary metal-oxide-semiconductor (CMOS) camera, such as a "camera on a chip" type CMOS imager specified by Given Imaging Ltd. of Israel and designed by Photobit Corporation of California, USA. In alternate embodiments, the imager 46 may be another device, for example, a charge-coupled device (CCD).

The illumination source 42 may be, for example, one or more light emitting diodes, or another suitable light source.

In operation, imager 46 may capture images and send data representing the images to transmitter 41, which transmits images to receiver 12 using, for example, electromagnetic radio waves. Receiver 12 may transfer the image or other received data to storage unit 16. After a certain period of time of data collection, the image data stored in storage unit 16 may be sent to the data processor 14 (e.g., contained within workstation 2) or the data processor storage unit 19. For example, the image receiver storage unit 16 may be taken off the patient's body and connected to the personal computer or workstation 2 which includes the data processor 14 and data processor storage unit 19 via a standard data link, e.g., a serial or parallel interface of known construction. The image data may then be transferred from the image receiver storage unit 16 to the image database 10 within data processor storage unit 19.

Data processor 14 may analyze the data, for example, according to the logical editing database 20, and provide the analyzed data to the image monitor 18, where for example, a health professional views the image data and/or corresponding analyzed data such as contraction information or a computer-generated diagnosis. Data processor 14 may operate software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, or manipulated or analyzed. Data processor 14 may use the images to diagnose pathological conditions of for example the GI tract, and, in addition, the system may provide information about the location of these pathologies. While using a system where the data processor storage unit 19 first collects data and then transfers data to the data processor 14, the image data is not viewed in real time, other configurations allow for real time viewing.

According to one embodiment, the imaging device 40 may collect a series of still images as it traverses the GI tract. The images may be later presented as, for example, a stream or sequences of images or a moving image of the traverse of the GI tract. The in-vivo imager system may collect a large volume of data, as the imaging device 40 may take several hours to traverse the GI tract. The imager 46 may record images at a rate of, for example, four to forty images per second (other rates, such as two frames per second, may be used). The imager 46 may have a fixed or variable frame capture and/or transmission rate. When the imager 46 has a variable or adaptive frame rate (AFR), the imager 46 may switch back and forth between frame rates, for example, based on parameters, such as the imaging device 40 speed, estimated location, similarity between consecutive images, or other criteria. A total of thousands of images, for example, 50,000 images, may be recorded. The image recordation rate, the frame capture rate, the total number of images captured, the total number of images selected if the moving image is edited, and the view time of the moving image, may each be fixed or varied.

The image data recorded and transmitted by the imaging device 40 may be digital color image data, although in alternate embodiments other image formats may be used. In one example, each frame of image data may include 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19. The stored data may include one or more pixel properties, including color and brightness.

While information gathering, storage and processing are described to be performed by certain units, the system and method of the present invention may be practiced with alternate configurations. For example, the components gathering image information need not be contained in an imaging device, but may be contained in any other vehicle suitable for traversing a lumen in a human body, such as an endoscope, stent, catheter, needle, etc.

Data processor storage unit 19 may store a series of images recorded by an imaging device 40. The images the imaging device 40 records as it moves through a patient's GI tract may be combined consecutively to form a moving image stream or video.

Figure 2:
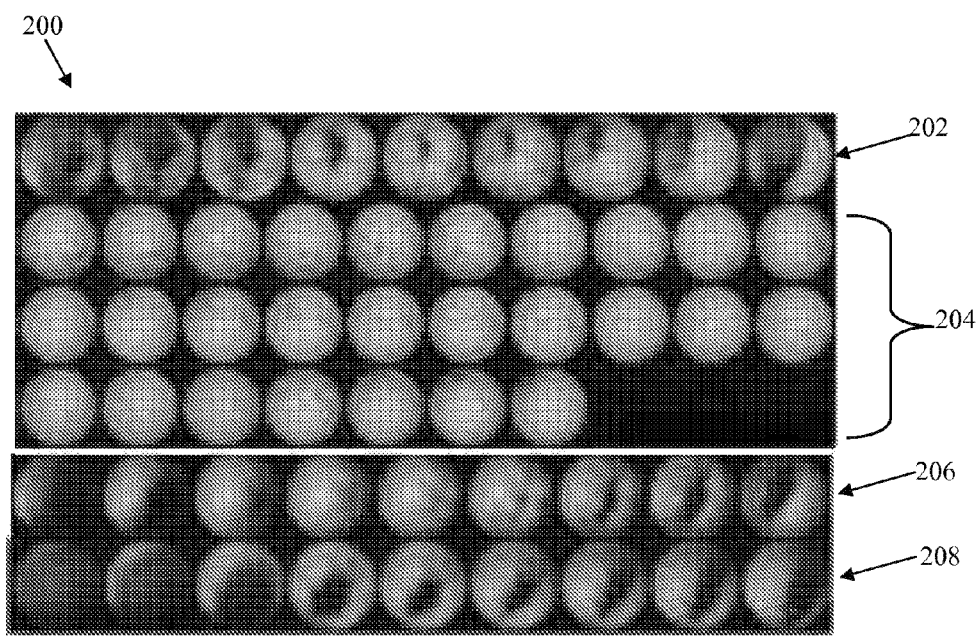
FIG. 2 shows images of template contraction sequences, according to embodiments of the present invention.

A moving image stream captured by the imaging device 40 may include scenes (e.g., a series of images depicting an event or the traversal of a particular region) or image sequences depicting predetermined or predicted events such as contractile activity of the body lumen walls (e.g., as shown in FIG. 2).

Data processor 14 may include a detection module 22 for automatically detecting predetermined sequential events, e.g., contraction scenes, using storage unit 19, an image database 10 and a logic detection database 20. Storage unit 19 may store images captured by imaging device 40. Image database 10 may store template or model contraction sequence(s) each associated with a unique set of contraction data or other known in-vivo events or scenes (e.g., such as the contraction events shown in FIG. 2). Logical detection database 20 may store instructions for execution or rules for use by software for comparing captured image(s) from storage unit 19 with the template sequence(s) from image database 10. Detection module 22 may use pattern recognition and/or feature extraction logic (for example, from logical detection database 20) to compare captured image frame sequences with template sequences and for example, detect a size and/or shape of the lumen opening in each frame.

Detection module 22 may be a physical device or may be instructions stored in a memory which when executed by a processor, e.g., data processor 14, may perform detection functions. For example, detection module 22 may be executed by a separate processor or may be a dedicated processing module.

Reference is made to FIG. 2, which shows images of template contraction sequences 200, according to embodiments of the present invention. Template contraction sequences 200 may be stored for example in storage unit 19 of FIG. 1.

Template contraction sequences 200 (e.g., a scene or series of images depicting a contraction event) may be a sequence of consecutive frames with pre-defined or pre-analyzed contraction or diagnosis data that serve as a reference bank, to which captured or query endoluminal scene sequences may be compared for identification and analysis of endoluminal contractions.

Template contraction sequences 200 may include, for example, phasic contractions, tonic (sustained) contractions, occlusive (fully closed) contractions, semi- or non-occlusive (partially closed), and a tunnel sequence (or no contraction). Template sequences 200 may include GI contraction patterns, such as small intestine (SI, also known as small bowel) contractions patterns, which may be among the contraction patterns which may bear clinical pathological significance for gastrointestinal disorders, such as ileus, bacterial overgrowth, functional dyspepsia and irritable bowel syndrome. GI template contraction sequences 200 may be classified in a number of ways to aid in diagnosis, for example, on the basis of their duration.

In the example shown in FIG. 2, template contraction sequence 202 (the $1^{st}$ row of images) shows a phasic contraction and template contraction sequence 204 (the $2^{nd}$ to $4^{th}$ rows of images) shows a tonic contraction. Phasic contraction sequences 202 are generally shorter (less time and/or fewer frames) than tonic contraction sequences 204. In one example, phasic contraction sequence 202 may include a sudden closing of the intestinal lumen, followed by a posterior opening. The duration of this open-closed-open sequence may be, for example, 4-5 seconds (e.g., corresponding to 8-10 frames at 2 frames per second or another number of frames at another frame rate). In contrast, tonic contraction sequence 204 is generally longer than phasic contraction sequence 202. In one example, tonic contraction sequence 204 may include a pattern of sustained closed lumen contraction images that may last for a relatively large period of time or number of frames (e.g., 27 at a frame capture rate of 2 fps in the example in FIG. 2). This pattern may be identified by the presence of wrinkles, such as, star pattern folds in the intestinal wall produced by sustained muscular tone, which may be identified by pattern-recognition mechanisms executed, for example, by data processor 14 of FIG. 1. An example of a system and method for wrinkle detection is disclosed in an embodiment in U.S. patent application Ser. No. 12/282,704, which is assigned to the common assignee of the present application and incorporated herein by reference in its entirety.

Template contraction scenes or sequences 206 and 208 show, for example, occlusive and non-occlusive contractions, respectively. Occlusive contraction sequence 206 includes a complete or substantially complete closing of the intestinal passageway having no opening or a substantially small opening (e.g., an opening not greater than a predetermined size or percentage of the image area, such as, <5%). Non-occlusive (or semi-occlusive) contraction sequences 208 include an incomplete closing or substantially opening of the intestinal lumen (e.g., the opening greater than or equal to a predetermined size or percentage of the image area, such as, 5%). In some embodiments, a frame may only be analyzed for occlusion if one or more of its neighboring frames follow the same contraction pattern, for example, so that dark spots, shadows or other visual artifacts or noise are not confused with a non-occlusive opening.

Each template contraction scenes or sequence 200 and the features therein (e.g., openings, wrinkles, etc.) may be selected or generated, for example, automatically using a computer recognition module or manually by a physician or program developer. Each template contraction sequence 200 may have pre-generated annotations associated therewith, for example, for identifying and diagnosing matching captured sequences.

Figure 3:
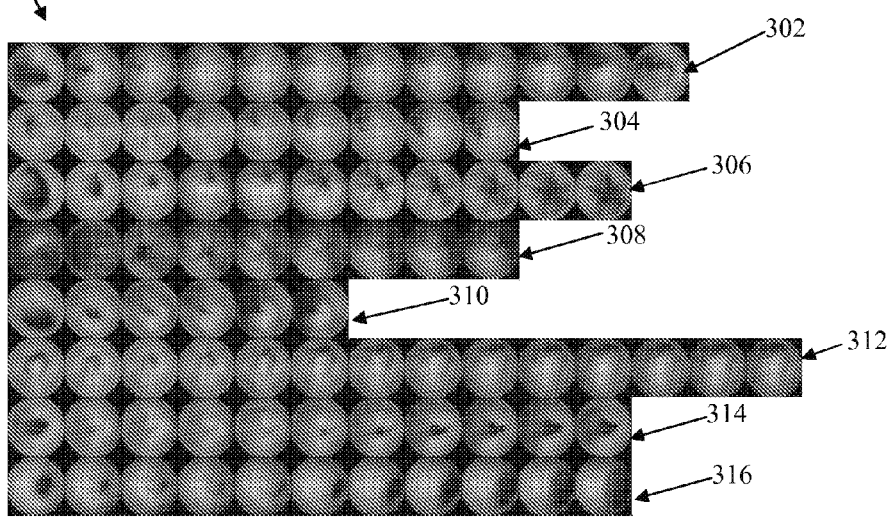
FIG. 3 shows images of captured in vivo sequences, according to embodiments of the present invention.

Reference is made to FIG. 3, which shows images of captured in vivo sequences, according to embodiments of the present invention.

Query or captured scenes or sequences 300 may be intestinal sequences identified as potential contraction sequences (e.g., by detection module 22 FIG. 1), but which are typically not associated with pre-analyzed contraction or diagnosis data. Captured sequences 300 may be compared with template contraction sequences for contraction analysis.

Captured sequences 300 may include sequences satisfying predetermined contraction criteria including, for example, having a center frame with a local minimum sized lumen opening associated with a (complete or partial) closing of the lumen passageway (e.g., below a predetermined threshold maximum size or above a predetermined threshold minimum percentage of size reduction), a predetermined rate of closings of the lumen opening, an open-closed-open lumen contraction pattern occurring within a predetermined period of time or number of frames (e.g., within 10 frames for phasic contractions and 30 frames for tonic contractions at a frame rate of 2 fps), or a predetermined periodic pattern or change in shape, size such as radius, diameter, area, or mass flow rate or other predetermined distortion of the lumen passageway. In some embodiments, the sequences may include events that depict a certain steady state in the gastrointestinal lumen, for example, tunnel event sequences or static sequences in which the lumen remains substantially open for a certain duration of time or closure event sequences in which the lumen may remain substantially (partially or completely) closed for at least predetermined period of time. A time stamp or frame number may mark or be associated with each captured image, for example, relative to the start of image capture or as an absolute time and/or date. Other or different criteria may be used for selecting captured sequences 300. A center frame of a sequence may be for example a frame having an equal or substantially equal number of frames before and after the frame in the sequence or, if the sequence is compressed, elongated, scaled, or otherwise distorted, the center frame may be the frame at the midpoint (e.g. in terms of time) of the scaled sequence. In case of asymmetric contractions, for example, the number of frames and/or time before and after the midpoint of the contraction (e.g., the frame with a minimum size lumen opening) may be different. An asymmetric contraction may include, for example, a relatively smaller number of frames and/or time before the midpoint of the contraction (e.g., less than one second for the closing of the lumen) and a relatively greater number of frames and/or time after the midpoint of the contraction (e.g., greater than 5-6 seconds for the opening of the lumen).

Some or all of captured sequences 300 of FIG. 3 may be compared to one or more of template contraction sequences 200 of FIG. 2 and may be assigned the contraction or diagnosis data of the specific template contraction sequences 202-208 if a match is detected therebetween.

Since sequences 200 and 300 are selected or extracted to show anatomical events or scenes which vary in duration, processing devices or processes operating in accordance with embodiments of the invention may be configured to input and compare captured sequences 300 and template contraction sequences 200 having different (or the same) numbers of frames. Frames in sequences 200 and 300 may be aligned for comparison (e.g., as described in reference to FIG. 4).

In some embodiments, a predetermined error threshold may be allowed for detecting a match between template sequences 200 and captured sequences 300. In one embodiment, a match may be detecting when all but a predetermined number of correlated frames in sequences 200 and 300 match.

In another embodiment, a match may be determined when all correlated frames in sequences 200 and 300 match except those in a predetermined sequential order. For example, the first and/or last frame(s) in sequences 200 and 300 need not match but the respective center frames in sequences 200 and 300 may be required to match. In another embodiment, the processor may compute a weighted sum of the error or difference between sequences 200 and 300, in which one, multiple, or all frames in a specific order are given a different weight. For example, the difference between the center frames in sequences 200 and 300 may have the greatest error weight and the difference between the first and last frames in sequences 200 and 300 may have the smallest error weights and all other frames may have error weights therebetween. The difference between correlated frames in sequences 200 and 300 may be calculated, for example, based on the differences between the lumen sizes associated with the correlated frames. In some embodiments, the distance of the imaging device from the imaged tissue may be estimated, for example, based on the illumination level of the pixels, and a relative or actual size of the lumen may be calculated based on the distance estimation, and the difference between lumen sizes may be normalized accordingly.

When a near threshold match is found between sequences 200 and 300, data processor 14 may mark or flag the sequence for secondary processing or human inspection via monitor 18 and input device 24. The secondary processing may be relatively more computationally intensive as compared to the aforementioned analysis, analyzing additional information including local and/or global trends in capsule motility or searching a secondary larger database of additional template contraction sequences for a match. In one embodiment, secondary processing may only be used when aforementioned analysis generates uncertain results, for example, to preserve computational resources. The threshold allowable error range may be set and/or adjusted, for example, increased to minimize contraction evaluation processing effort or decreased to maximize contraction evaluation accuracy.

As a capsule travels through the GI tract, obstructions, foreign substances, visual artifacts, irregularity in capsule speed, field of view or frame capture rate, diversity in anatomical events and other factors may cause irregularities in images captured by the capsule. Such irregularities in the captured images, although often easily recognizable to a human operator, may be very difficult for an automated decision-making processing machine to compare to a predetermined set of template images. An adaptive processing system and method is provided according to embodiments of the invention, to identify unwanted irregularities in order to optimally and automatically compare (e.g., without human intervention) the anatomical objects and contractions in the captured and template sequences.

In one embodiment, data processor 14 may automatically analyze a video stream captured in vivo to identify and categorize contractions by tracking and comparing changes in the size of the lumen passageway in the template and captured sequences 200 and 300. Since the lumen passageway is an easily recognizable structure that extends over a wide pixel area in images, by measuring the passage size, visual obstructions may interfere minimally with the sequence comparison. Data processor 14 may align frames (e.g., mark a correspondence) between sequences for comparison with the most similar lumen size changes and/or other contraction identifiers to get a best overall fit or smallest total difference. Comparing sequences with frames aligned based on the opening or closing of the lumen passageway may reduce the effect of irregular capsule speed, for example, as compared with a conventional one-to-one frame alignment. In one embodiment, all captured frames (even those later removed by turbid or static filters) may be used to align the captured and template sequences. Alternatively, the turbid or static filters may first remove turbid or static frames from the captured image stream and filtered captured sequences 200 may then be aligned with the template sequences 300.

Further irregularities in the camera orientation or field of view in which the camera points away from the lumen opening may hide or obscure contraction events. In such embodiments, a contraction may be identified by deducing or extrapolating results from other adjacent frames in the captured sequence 300 or from the partial curvature of the passageway in the current frame if the lumen opening is at least partially imaged.

In one embodiment, data processor 14 may (1) measure lumen sizes in a captured image stream and generate a function of the lumen size of the captured sequences 300; (2) generate a model or input a pre-generated model function of the lumen size of template contraction sequences 200, and (3) search for matching patterns of the lumen size functions of template contraction sequences 200 and captured sequences 300. The processor may automatically match the most similar one or more of the plurality of captured sequences 300 to each template contraction sequence 200. The processor may automatically assign the captured sequences 300 the contractile and/or motility data or metadata (e.g., the type of contraction, the duration of the contraction, ratio of contraction symmetry and asymmetry, etc.) pre-associated with the matching template contraction sequence 202-208.

The contraction data assigned to each captured sequences 302-316 may be used, for example, to automatically characterize contractions and diagnose gastrointestinal motility disorders in the patient from which the images were captured. Diagnosis of pathology and/or disorders may be based on, for example, number, size, frequency, distribution, symmetry, duration and/or geometrical pattern of contractions along the intestinal tract. Other aspects of contractile activity may be inspected.

Contractile activity or sequences in a captured image stream may be tagged, flagged, marked, or otherwise indicated (and may be added to frames or sequences of frames as, e.g., metadata). For example, graphical markers along a time bar or tissue color bar may visually indicate where along an image stream or in the GI tract image frames including contractile activity have been identified. In another example, hidden or non-visual markers, such as flags in a data register or cache, or with metadata associated with frames, may indicate contractile frames or segments in the image stream. In some embodiments, data processor 14 may automatically skip to the indicated frames for processing and/or a monitor may automatically skip to display the indicated frames. For example, a user may choose to view only segments or sequences which were found as correlating to one or more predetermined template contraction sequences. Other methods of identifying image frames depicting contractile activity may be used.

Data processor 14 of FIG. 1 may use detection module 22 and logic from logic editing database 20 to align and compare captured sequences 300 of FIG. 3 with template sequences 200 of FIG. 2, and/or to identify patterns or trends having a pre-defined correlation with intestinal motility characteristics. For example, if a captured sequence 300 matches a template sequence 200 of, for example, a slow sequence of contractions (the intestinal passageway opens and closes with a slow periodicity), then the motility of the captured sequence 300 may be defined to be slow.

However, as discussed, additional factors may affect the correct alignment and matching of captured sequence 300 and template sequence 200. Factors may include, for example, the direction or degree of contraction deformation, the speed of the imaging device, and imaging artifacts, such as contraction events not captured that occur in-between consecutive images, that are blocked by bubbles, or that are not in the imager field of view.

Data processor 14 may assign a lumen size value to each image and correlate images with similar lumen size values, for example, using pointers or indices. By aligning images in a sequence based on extracted anatomical features, such as lumen size, instead of using a one-to-one comparison, embodiments of the invention may bypass imaging artifacts due to irregularities in the motion of the imaging device or visual obstructions.

In one embodiment, data processor 14 may assign one or more values or scores to rank the lumen size in each of one or more frames of the template and captured sequences 200 and 300. The processor may determine the differences between lumen size scores assigned to each frame in the captured sequence 300 and each of a plurality of frames in the template sequence 200. The processor may determine the alignment between frames in the template and captured sequences 200 and 300 that minimizes the overall or cumulative difference in lumen size scores throughout the sequences 200 and 300. This transformation may optimally align the sequences 200 and 300 by aligning the most similar frames using scores associated with the size of the lumen opening in the frames, the change in size of the lumen opening between frames, and other factors affecting image motion. Thus, the true anatomical spacing of in vivo objects, not artifacts such as irregular imager motion, may determine the frame alignment.

In some embodiments, data processor 14 may align or correlate multiple frames of the captured sequence 300 to a single frame of the template sequence 200, or vice versa. These transformations may provide a many-to-one or one-to-many correspondence, respectively, between frames of the template and captured sequences 200 and 300. The correspondence type may fluctuate within the length of an individual captured sequence 300 or between consecutive captured sequences 300 through the length of the entire image stream.

Data processor 14 may align frames in a sequence to preserve the order of the frames in their original non-aligned sequences 200 and 300. For example, if a frame (n) from the captured sequence 300 is aligned with a frame (m) from the template sequence 200, a subsequent frame (n+1) from the captured sequence 300 may only be aligned with the same and/or subsequent frame(s) (m), (m+1), (m+2), ..., but not with a preceding frame (m−1) from the template sequence 200.

Once captured sequences 300 are found that best match each template sequence 200 in the image stream, data processor 14 may compile and analyze the associated contraction data. The processor may input the contraction data into a detection module (e.g., detection module 22 of FIG. 1), which may automatically identify contractions or other events, and may determine a diagnosis based on statistical analysis of the contraction data. The processor may assign the computer-determined diagnosis to the captured in vivo images.

The captured image stream, the contraction data and/or the automatic diagnosis data may be displayed to a user, for example, on a digital display screen (e.g., monitor 18 of FIG. 1).

Figure 4:
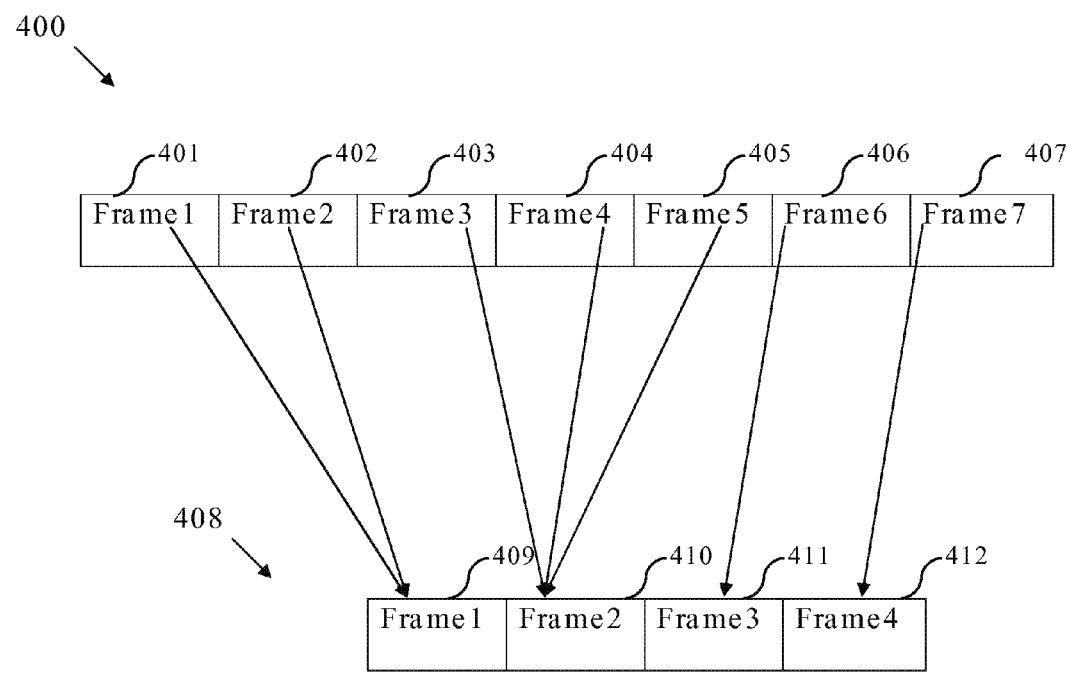
FIG. 4 is a schematic illustration of an alignment between a captured sequence and a template contraction sequence, according to an embodiment of the invention.

Reference is made to FIG. 4, which schematically illustrates an alignment between a captured sequence 400 and a template contraction sequence 408, according to an embodiment of the invention.

In one embodiment, data processor 14 may apply criteria (e.g., selected from logic database 20 of FIG. 1) to divide the image stream into sequences such as sequence 400. In one example, the processor may divide sequences beginning and ending (e.g., at frames 401 and 407) with an opening of the lumen passageway and including a center frame (e.g., frame 404) with a complete or partial closing of the lumen passageway. The rate of the opening and closing of the lumen passageway may determine the lengths of the captured sequences 400.

Data processor 14 may synchronize or align captured sequences 400 and template sequences 408 using a map or transformation 414 aligning frames 401-407 and frames 409-412 to minimize the cumulative "energy" or difference in lumen size scores or values between the frames. To determine the optimal or minimum energy map 414, the processor may compare each frame in the captured sequence with each frame or a plurality of frames in the template sequence 408 based on a plurality of predetermined criteria. Individual frames or sets of frames in one sequence may be linked to frames or sets of frames in the other sequence, e.g., using a pointer, a record in a database including correlated frames or sets of frames, or another method.

Figure 5:
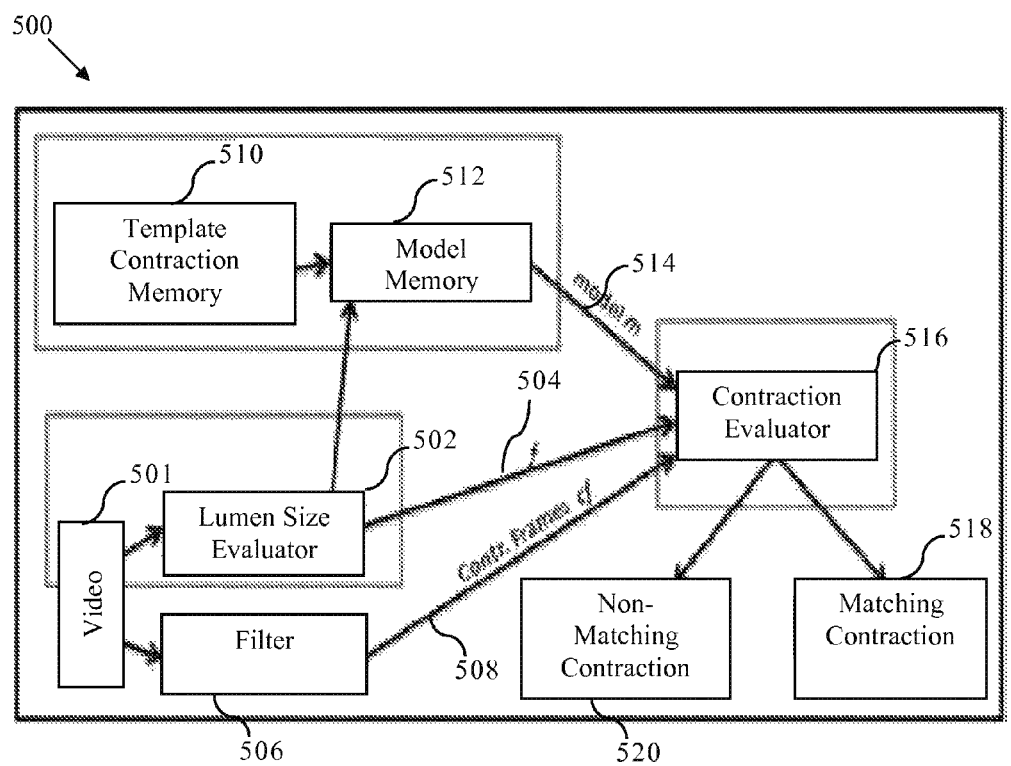
FIG. 5 is a schematic illustration of a data structure for comparing a captured sequence with a template contraction sequence, according to an embodiment of the present invention.

Reference is made to FIG. 5, which schematically illustrates a system 500 for comparing a captured or "query" sequence with a template or "model" contraction sequence, according to an embodiment of the present invention. System 500 may be contained within or may be operably connected to workstation 2 of FIG. 1.

A processor (e.g. data processor 14 of FIG. 1) may retrieve an image stream or video file 501 including a plurality of captured images (e.g. from storage unit 19 of FIG. 1).

The processor may include a lumen size evaluator module 502 to evaluate the lumen sizes of each captured frame. The lumen size of each frame may be defined by the number of pixels or the sum of values of pixels within the boundary of the lumen passageway. Pixels within the passage boundary may be detected that have an above threshold value on a gray scale of the image. Pixels on the boundary may be considered in the lumen passageway, for example, if more than a predetermined number of neighboring pixels are in. Alternatively, the lumen size may be defined by a radius, a diameter, a circumference, a vector of for example vertical, horizontal, and/or diagonal diameter(s), a two-dimensional surface or shape, or by a copy of the lumen passage image portion itself. Lumen size evaluator module 502 may use an estimation of the distance between the imaging device and the imaged tissue to transform the number of pixels into actual or normalized size estimation, e.g., in units of square millimeters, square inches, etc. The distance between the imaging device and the imaged tissue may be calculated using the focal length of the imaging lens, for example, defining the distance between the imaging lens and in-focus objects. A lumen size memory 504 may store data values for a function, $f$, describing an absolute or relative change in lumen size between every captured frame and another frame (e.g., the previous captured frame, a reference frame, or an aligned template frame).

The processor may include a filter 506 to extract a subset of frames, cf, that have locally minimum sized lumen openings. These frames, cf, may have maximum occlusion of the lumen passageway associated with a closing of the lumen in a contraction. A contraction frame memory 508 may store pointers, indexes or addresses identifying the extracted local minimum lumen opening frames or alternatively, may store the frames themselves.

A template contraction memory 510 may store one or more template contraction sequences (e.g., template contraction sequences 200 of FIG. 2), for example, and pre-generated annotations describing each imaged contraction.

The lumen sizes of each frame in each template contraction sequence may be measured (e.g., by lumen size evaluator module 502) or pre-generated (e.g., retrieved from template contraction memory 510) as a model function, m, defining an absolute or relative change in lumen size between every captured frame in the template contraction sequence and another frame (e.g., the previous template frame, a reference frame, or an aligned template frame). A model memory 512 may store the lumen size values of model, m. In one example, lumen size evaluator module 502 may calculate the values of model, m, to be median value from corresponding frames of all template contraction sequences (e.g., which may be normalized to values from 0 to 1).

A contraction evaluator module 516 may compare the functions, $f$ and m, defining the changes in lumen size for sequences of frames in the captured video (e.g., captured sequences 300 of FIG. 3) and template contraction sequence, respectively. Since a lumen passageway is typically open at the beginning and end of a contraction and a lumen is typically (partially or completely) closed at or near the center of a contraction, contraction evaluator module 516 may compare the model, m, to segments of lumen size function, $f$, beginning and ending at local maximum values of function, $f$, (e.g., open passageways) and centered at local minimum values of function, $f$, for local minimum frames, cf, (e.g., narrowing or closed passageways). These segments of lumen size function, $f$, associated with an open-closed-open lumen passageway pattern typical of contractions are more likely than other segments to exhibit contractions and match the lumen size patterns of model, m.

The contraction evaluator module 516 may identify matching contraction sequences associated with segments of lumen size functions, $f$, that differ from the lumen size model function(s), m, by less than a predetermined threshold. The difference between segments of lumen size functions, $f$, and a model function, m, may be, for example, a sum of absolute differences (SAD) or mean or standard deviations (SD) therebetween. In some embodiments, the lumen size difference(s) may be weighted for each frame. For example, the difference(s) between the minimum lumen size values (e.g., of a center frame) and/or the maximum lumen size values (e.g., of first and last frames) may have greater weight(s) in the difference calculation than other mid-range lumen size values to prioritize similarities at the closing and/or opening stages of the contractions, respectively. Other difference or error calculations may be used.

A matching contraction memory 518 may store indexes, pointers or addresses identifying the frames of the matching contraction sequences or may store the frames themselves. A non-matching contraction memory 520 may store indexes, pointers or addresses identifying all other evaluated frames or a subset of frames explicitly determined to be non-matching contractions. In one embodiment, matching and non-matching sequences may be mutually exclusive subsets, which, when combined form the complete set of evaluated frames. In another embodiment, some evaluated sequences may be neither matching nor non-matching frames, for example, when the difference between the lumen size function $f$ of the frame and the lumen size model function, m, is substantially near or equal to a difference threshold (e.g., within 2%).

Video 501, lumen size memory 504, contraction frame memory 508, template contraction memory 510, model memory 512, matching contraction memory 518 and non-matching contraction memory 520 may be in workstation 2 of FIG. 1, for example, in storage unit 19, image database 10, and/or a memory internal to data processor 14. Lumen size evaluator module 502, filter 506, and contraction evaluator module 516 may be in workstation 2 of FIG. 1, for example, in detection module 22; data processor 14 which effects the functionality of these and other modules by executing instructions from logical editing database 20.

Figure 9:
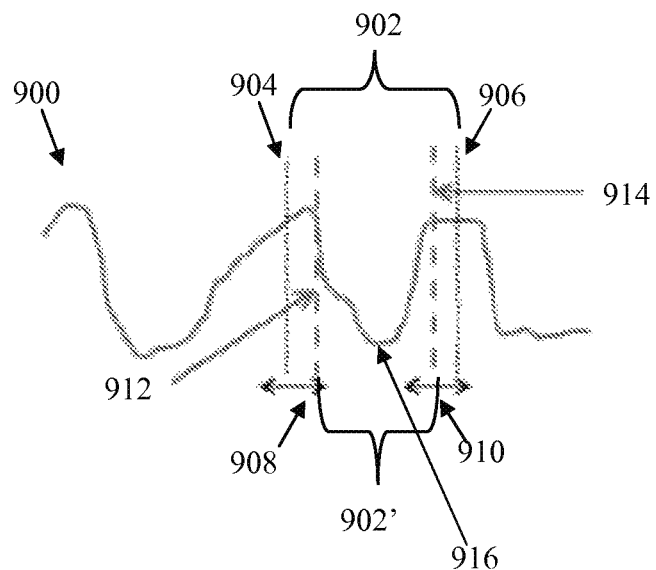
FIG. 9 is a graph of the lumen size of a detected contraction sequence, according to an embodiment of the present invention.

Once the matching contraction sequences are identified, the processor may analyze and characterize these contraction sequences (e.g., as described in reference to FIG. 9).

Figure 6:
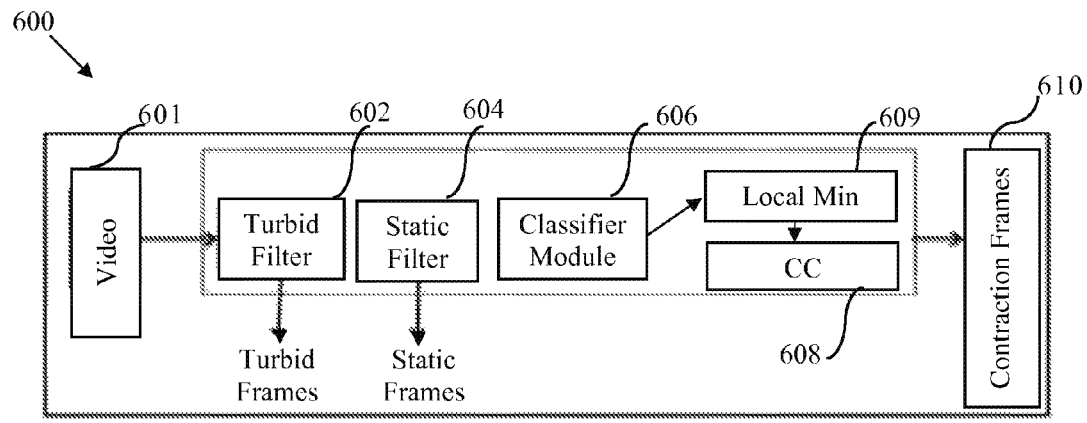
FIG. 6 is a schematic illustration of a data structure for filtering a subset of video frames, according to an embodiment of the present invention.

Reference is made to FIG. 6, which schematically illustrates a system 600 for filtering a subset of video frames, cf, according to an embodiment of the present invention. System 600 may be contained within or may be operably connected to workstation 2 of FIG. 1.

A filter 600 (e.g., filter 506 of FIG. 5) may input a set of frames or a video 601 captured in vivo and output a subset of frames 610 thereof that satisfy predetermined criteria. Filter 600 may remove or ignore obstructed or distorted frames and extract or identify a subset of frames having locally minimum sized lumen openings.

Filter 600 may include a turbid filter 602 to remove frames with an above threshold amount of turbid or other visual obstructions in the frames. Filter 600 may include a static filter 604 to remove static frames with a below threshold movement or change between adjacent frames in the captured image stream. These frames may be captured while the capsule is static or moving below a minimum threshold speed. Since contractions typically propel and move the capsule, contractions are unlikely to be present in static frames and their removal prior to searching for contraction frames with minimum sized lumen openings may save significant computational effort. The thresholds for turbid and static filters 602 and 604 may be set or adjusted, for example, increased to decrease the number of extracted frames and processor effort for analyzing those frames or decrease to increase the number of extracted frames and processor effort. In one embodiment, a user may select one or more frame(s) having the minimum allowable (or maximum not allowable) turbid, obstructions, distortions or visual artifacts and the processor may automatically set the threshold levels for contractions accordingly. In some embodiments, static captured or query sequences may also be compared to static template sequences. For example, finding more than a predetermined number of static sequences in an image stream of a patient may indicate, for example, motility dysfunction or insufficient contractile activity of the patient's GI tract.

Filter 600 may include a classifier module 606 for assigning classifiers, such as support vector machine (SVM) classifiers, to one or more frames in video 601, for example, not removed by filters 602 and 604.

Classifiers may assign a value, rank or score for a type or class of contraction, for example, a normalized value or range of the size of the lumen opening, whether or not a frame is associated with a contraction, whether or not a contraction achieves full occlusion (complete closing of the passageway), whether or not a contraction is phasic, whether or not a contraction is symmetric, whether or not a frame is a center frame, whether or not a frame is a boundary frame (e.g., a first or last frame) of a sequence, whether or not a frame has a locally maximum lumen size, whether or not a frame has a locally minimum lumen size, etc. In one embodiment, classifier module 606 may assign a score within a first predetermined range (e.g., positive values) to frames having a greater than threshold lumen size opening and a score within a second predetermined range (e.g., negative values) to frames 610 (e.g., or to frames in the same sequence as such a frame) having a below threshold or minimum lumen size opening. Frames with a below threshold or minimum lumen size opening (e.g., a negative classifier score) may be associated with the closing of the lumen passageway and potentially, may be part of a contraction sequence.

In one embodiment, classifier module 606 may assign classifiers to each frame independently, or to multiple frames in a sequence together. In one embodiment, classifier module 606 may analyze sequences having an equal predetermined length (e.g., nine (9) frames including a center frame, four (4) previous and four (4) subsequent consecutive frames). The predetermined length of the analyzed sequences may depend on the frame capture rate or the deletion of any filtered or dropped frames. For example, classifiers are assigned to sequences with a relatively large number (e.g., 18) frames when a relatively larger frame capture rate (e.g., 40 fps) is used and classifiers are assigned to sequences with a relatively small number (e.g., 9) frames when a relatively small frame capture rate (e.g., 2 fps) is used. Alternatively, the predetermined length of the analyzed sequences may not depend on the frame capture rate. In another embodiment, classifier module 606 may analyze sequences having varying lengths. In one example, the lengths of the sequences may alternate between different predetermined lengths associated with different contraction types. In another example, the lengths of the sequences may be based on the lumen size patterns of the frames. For example, classifier module 606 may sequentially assign classifiers to consecutive frames until classifier module 606 cycles through values for a maximum-minimum-maximum lumen sizes (e.g., corresponding to an open-closed-open lumen contraction pattern). Other classifier scores, ranges, frame capture rates and sequence partitions may be used.

Filter 600 may include a connected component 608 to join neighboring or consecutive frames having negative or local minimum classifier scores (e.g., potentially part of a contraction) into one sequence, data block, or connected component. Filter 600 may include a local minimum module 609 to identify each frame (e.g., of each connected component) having a minimum lumen size or classifier value. Connected component 608 and local minimum module 609 may output indexes, pointers or other identifiers of the local minimum lumen size frames, their lumen sizes or classifier scores, and/or the frames 610 themselves.

In one embodiment, filter 600 may remove distorted frames reducing the volume of frames to be analyzed for contractions and may isolate frames with a local minimum sized lumen opening, which are most likely to be part of a contraction. In some embodiments, a contraction evaluator (e.g., contraction evaluator 516 of FIG. 5) may only analyze captured frames filtered by turbid or static filters 602 and/or 604 or may only analyze captured sequences centered at or including a local minimum lumen size frame identified by local minimum module 609. In other embodiments, the contraction evaluator may also analyze frames not selected by filter 600, but only after evaluating the selected frames 610, or with lower priority, using different threshold parameters, or using different template contraction sequences than are used for the selected frames 610.

Video 601 and contraction frames 610 may be stored in workstation 2 of FIG. 1, for example, in storage unit 19, image database 10, and/or a memory internal to data processor 14. Filter 600, turbid filter 602, static filter 604, classifier module 606, connected component 608 and local minimum module 609 may be in workstation 2 of FIG. 1, for example, in detection module 22; or in data processor 14, which effects the functionality of these and other modules by executing instructions from logical editing database 20.

Figure 7:
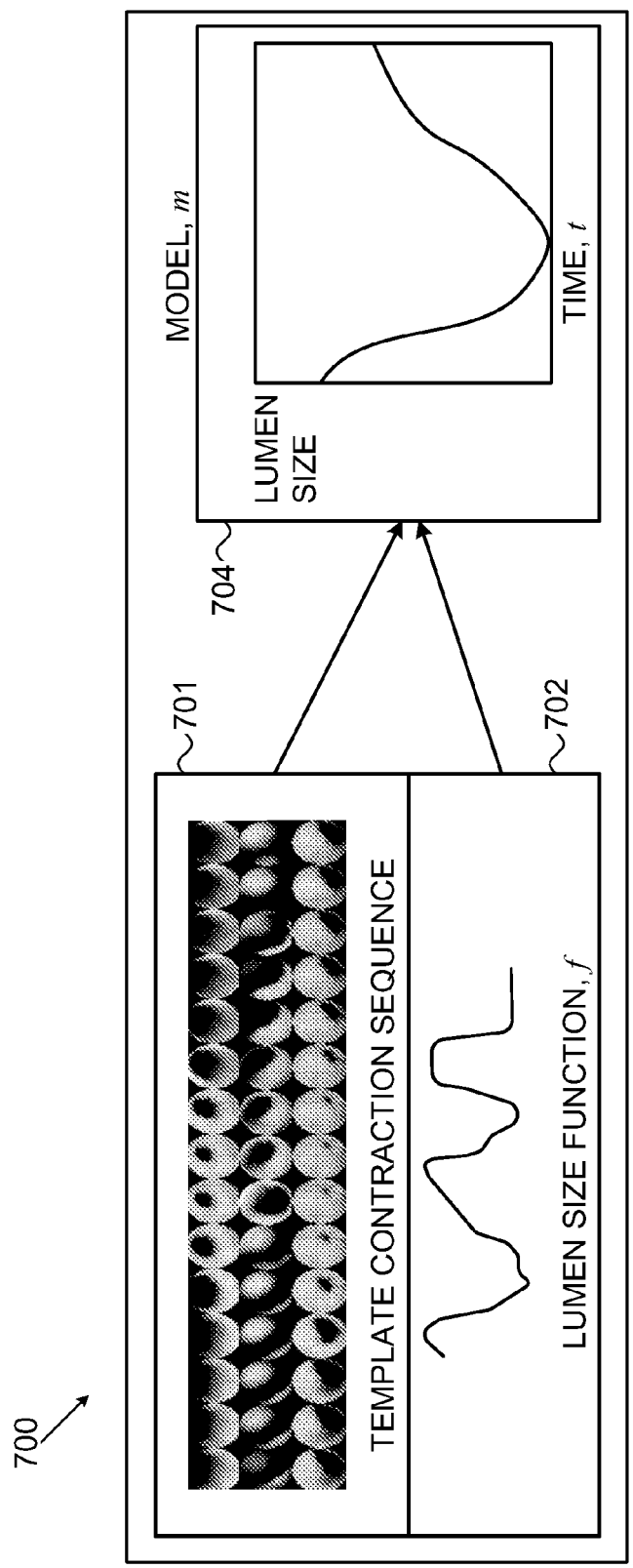
FIG. 7 is a schematic illustration of a data structure for generating a model of the lumen size of a template contraction sequence, according to an embodiment of the present invention.

Reference is made to FIG. 7, which schematically illustrates a system for generating a model, m, of a lumen size function of a template contraction sequence, according to an embodiment of the present invention. System 700 may be contained within or may be operably connected to workstation 2 of FIG. 1.

A template memory contraction memory may store one or more template contraction sequences 701 (e.g., template contraction sequences 200 of FIG. 2), for example, selected by an expert and/or associated with pre-generated annotations in a product development phase.

A lumen size evaluator module may generate a model 704 including the lumen sizes of each frame in template contraction sequences 701 of images. The lumen size model 704 may be, for example, a median value of lumen sizes for aligned frames in the same order in other sequences. For example, the first lumen size value of model 704 may be the median of all the values of the aligned first frames in all the template sequences, the second value of model 704 being the median of all the values of the aligned second frames in all the template sequences, etc. The median value may be computed from lumen sizes associated only with marked or identified contractions (e.g., which may be normalized to values from 0 to 1).

A lumen size memory may store data values for a function 702 describing the lumen sizes of frames in an input video stream. Function 702 may be used to determine the partition of the image stream into sequences and thus, which sequences of the input video to compare to the model 704.

Figure 8:
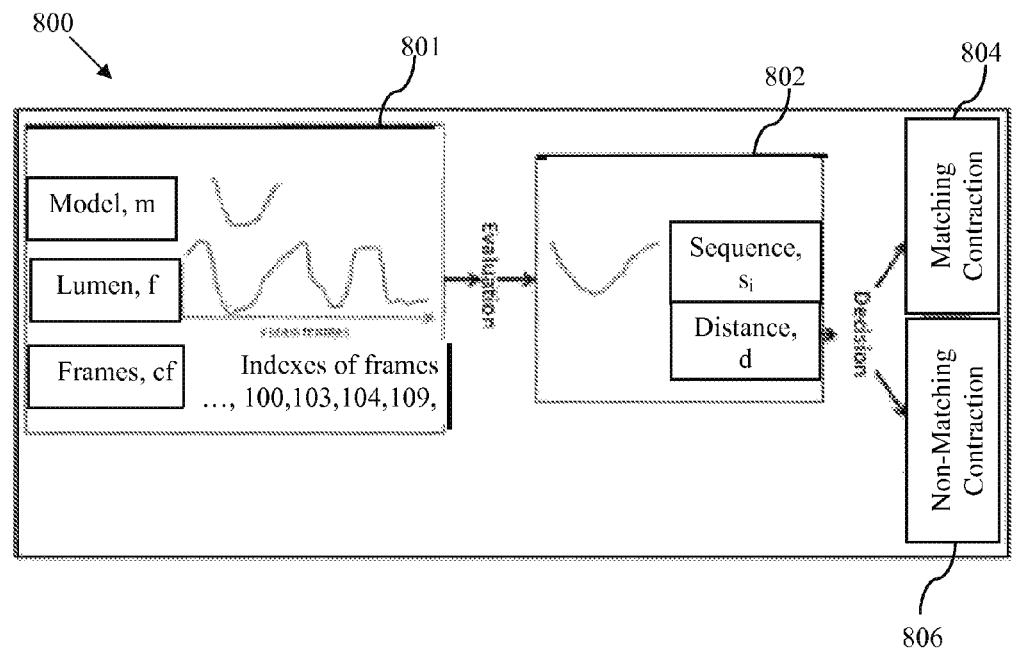
FIG. 8 is a schematic illustration of a data structure used for detecting contraction sequences, according to an embodiment of the present invention.

Reference is made to FIG. 8, which schematically illustrates a system for detecting matching contraction sequences, according to an embodiment of the present invention. System 800 may be contained within or may be operably connected to workstation 2 of FIG. 1.

One or more memory unit(s) 801 may store a template or model function, m, lumen size function, $f$, and/or indexes, cf (e.g., in model memory 512, lumen size memory 504, and contraction frame memory 508, respectively). Model m, may define a change in the lumen size associated with each frames in a template contraction sequence. Lumen size function, $f$, may define a change in the lumen size associated with each frame in the captured image stream. Indexes, cf, may define a subset of frames of the captured image stream file (e.g., extracted by filter 506 of FIG. 1) that have a local minimum size lumen opening. Frames with indexes, cf, may correspond to a (partial or complete) closing of the lumen wall, which often occurs at or near the center of each contraction. Accordingly, each query or captured sequence may be centered at or near a frame of index, cf.

A contraction evaluator module 802 (e.g., contraction evaluator module 516 of FIG. 5) may receive the template or model function, m, the lumen size function, $f$, and indexes, cf, to extract matching contractions from a video or image stream file. For each local minimum frame, i, in the set of local minimum frames of indexes, cf, contraction evaluator module 802 may generate a plurality of lumen size sequences, $s_i$, of segments of the lumen sizes function, $f$, of different lengths including or centered about the same minimum lumen size value of frame, i. Each of the plurality of lumen size sequences, $s_i$, may differ in the number of consecutive frames before and after the local minimum value, for example, growing outward in length from the center minimum value. Contraction evaluator module 802 may analyze lumen sizes sequences, $s_i$, for a corresponding plurality of captured frame sequences of different lengths to detect contractions of varying lengths. In one example, for each frame, i, contraction evaluator module 802 may generate lumen size sequences, $s_i$, for an integer number of frames, n=2, . . . , 12, on each side of frame, i, for example, generating sequences with lumen size values for an odd number of frames from five (5) (e.g., a typical phasic contraction at a frame rate of 2 fps) to 25 (e.g., a typical tonic contraction at a frame rate of 2 fps) and providing a total of 11 sequences, $s_i$. Other numbers of frames, values, sequences, and frame capture rates (fps) may be used, for example, according to the type of contraction sought.

The processor may scale each of the captured lumen size sequences, $s_i$, with the template lumen size sequence, m, for example, to generate a single or equal length lumen size sequences regardless of the number of frames valued by the respective sequences. As the lengths of the lumen size sequences, $s_i$, increase, the mapping to the same template lumen size sequence, m, of the same length may become increasingly compressed.

The processor may align each captured sequence with the template sequence by for example correlating the most similar corresponding lumen size values in sequences, $s_i$ and m, for example, to generate a minimum cumulative difference between all correlated lumen size values. Accordingly, frames with similar sized lumen openings in the sequences may be correlated so that the lumen size sequences are aligned based on the opening and closing of the lumen passage. Multiple frames in one of sequences $s_i$ and m may correlate to a single frame in the other one of the sequences, for example, generating a "one-to-many" or "many-to-one" correlation. Frame alignment may preserve sequence order, for example, so that the order of the frames to which a sequence is aligned is consistent with the order of the frames in that sequence.

In one embodiment, the processor may generate a "distance" function, $d_i$ at data structure 802 to measure the cumulative difference in the correlated lumen size values of each captured sequence, $s_i$ and template lumen size sequence, m, for example, using a dynamic time warping (DTW) mechanism. Each captured sequence, $s_i$, may be aligned to minimize the distance function $d_i$, for example, to minimize the cumulative lumen size difference with the template lumen size sequence, m, as compared to other alignments. The sequence, $s_j^{best}$, having the smallest distance function $d_{best}$ (e.g., the most similar cumulative lumen size difference compared to the template contraction sequence) may be selected for analysis from among the plurality of other sequences, $s_i$, centered around the center frame, i.

In one example, for a contraction with a relatively long duration (e.g., a tonic contraction), an optimal alignment may be found with a relatively long one of the plurality of sequences, $s_i$, and likewise, for a contraction with a relatively short duration (e.g., a phasic contraction), an optimal alignment may be found with a relatively short one of the plurality of captured sequences, $s_i$. Accordingly, contractions having a wide range of durations may be accurately analyzed and detected in the captured image stream.

Once the best matched captured lumen size sequence, $s_j^{best}$, is selected, the process or processor may determine if that captured sequence is sufficiently similar to the template lumen size sequence, m. The processor may compare the smallest distance function $d_{best}$ to an error threshold defining the maximum allowable difference between the cumulative lumen size differences between frames in the template and captured sequences. If the error between the template and captured sequences is sufficiently small (e.g., $d_{best} \leq$ threshold), the processor may automatically define a match therebetween. A match to a template sequence associated with a contraction may indicate the presence of a contraction in the captured sequence. The best matched captured sequences (or indexes thereof) that are less than or equal to the error threshold ($s_j^{best}$, $d^{best} \leq$ threshold) may be stored at a matching contractions memory unit 804 and the best matched captured sequences (or indexes thereof) that are greater than the error threshold ($s_j^{best}$, $d^{best} \leq$ threshold) may be stored at a non-matching contractions memory unit 806.

Embodiments described in reference to FIG. 8 may be implemented, in one example, by a processor (e.g., data processor 14 of FIG. 1) executing operations according to the following pseudo-code algorithm (although other operations may be used):

```
Function evaluate_contractions(f, m, cf, threshold, scale)
    For every index, i, of captured frame, cf:
        Prepare sequences sj from function f, of length from 5 to 25
            with a centre
            frame i, (from [f(i-2):f(i+2)] to [f(i-12):f(i+12)]).
        For every sequence sj:
            Scale sequence sj and model m to vectors of equal length sj' and
            m' (length(sj')==scale && length(m')==scale).
                Normalize sequences sj' and m' to values from 0 to 1.
                Calculate distance d=DTW(sj', m')/length(sj').
            Select the sequence sj^best with the best DTW fitting d^best.
        If (d^best≤threshold) then sj^best corresponds to a matching contraction.
end
```

Each of the parameters or inputs of the evaluate_contractions function ($f$, m, cf, threshold, and scale) may be adjusted to refine contraction identification.

The threshold parameter may define a maximum allowable difference between the lumen size sequences, $s_i$ and the model m, of the captured and template sequences. This threshold may be predefined or alternatively, may be variable or adjusted, for example, decreased to maximize contraction evaluation accuracy or increased to maximize the number of identified contractions. The threshold may be set or adjusted to permit different levels of distortion or error from perfectly matching a predefined template or model contraction. The threshold may define a decision border, delineating which frames match template contractions and which do not. For example, the threshold may be between 0.03 and 0.1, such as 0.04 or 0.06.

The scale parameter may define the lengths to which both the lumen size sequences, $s_i$ and the model m, are scaled or mapped. The scale parameter may be fixed as a predetermined scaling value, for example, 30, although other values may be used.

In some embodiments, lumen size sequences, $s_i$ may exclude filtered (e.g., turbid or static) frames. However, in some embodiments, to preserve the order, frame index number, and durations of sequences, the filtered frames may be used or may be replaced with place-holder frames (e.g., duplicated or averaged from other non-filtered adjacent frames). In other embodiments, filtered frames may be deleted and sequences previously including these frames may be re-aligned and re-indexed.

The distance $d_i$ may be a mean value of the differences in the positions of aligned frames in the respective template and captured sequence, $s_i$ with correlated lumen size values. For example, if the lumen size value of the $10^{th}$ frame in the captured sequence is compared to the lumen size value of the $18^{th}$ frame in the template sequence and the overall length of the captured sequence is 100 frames, the distance d may be the difference in the positions of the compared frames (10 and 18) divided by the overall length of the captured sequence (100). In this example, d=0.08, the mean difference between compared or correlated lumen size values in the sequences is 8% and the captured sequence is deformed by 8% to align with the template sequence. In other embodiments, the cumulative lumen size differences between frames in the template and captured sequences may be determined, for example, as a sum of absolute differences (SAD) or mean or standard deviations (SD) of the lumen size or pixel (e.g., color or gray scale) values of correlated frames in the respective sequences.

The contraction evaluation function may be adjusted by other parameters or values to define which sequences are matching contractions and which sequences are non-matching. Once the matching contraction sequences are identified, the processor may analyze and characterize the sequences, for example, as described in reference to FIG. 9.

Reference is made to FIG. 9, which is a graph used to evaluate matching contraction frames, according to an embodiment of the present invention.

The graph 900 may represent the lumen size function, $f$, of a segment or an entire captured video file.

A processor (e.g., data processor 14 of FIG. 1) may identify a lumen size contraction sequence 902 for a captured contraction matching a template contraction sequence (e.g., retrieved from matching contractions memory unit 804 of FIG. 8).

In one embodiment, the processor may refine the boundaries of the lumen size sequence 902 by adding or removing lumen size values before or after the first and last lumen size values 904 and 906. In one embodiment for removing lumen size values of frames, boundary windows 908 and 910 may identify lumen size values that are within a threshold range or percentage (e.g., 80-100%) of a maximum lumen size value for the sequence (e.g., corresponding to a substantially large opening of the lumen passage). Boundary windows 908 and 910 may span the same or different predetermined numbers of values (e.g., seven (7) of the first values) or may be set, for example, automatically based on the threshold range or manually via a user input signal. Lumen size values in boundary windows 908 and 910 may be removed from the beginning and end of lumen size sequence 902 to define a refined lumen size sequence 902' having refined beginning and end values 912 and 914. The processor may analyze lumen size sequence 902 or 902'.

The processor may define one or more center frame value(s) 916 of center frame(s) of sequence 902 or 902'. Center frame(s) may image an in vivo passage having maximal intestinal occlusion (e.g., or minimal lumen size).

The processor may use the beginning, center, and end values 912, 916, and 914, to generate the following contraction data for the matching contraction:

(a) contraction closing: a number of frames associated with values of sequence 902' between the beginning and center values 912 and 916.

(b) contraction opening: a number of frames associated with values of sequence 902' between the center and end values 916 and 914.

(c) duration of contraction: a number of frames associated with values of sequence 902' between the beginning and end values 912 and 914.

(d) duration of occlusion: a number of frames associated with the center value(s) 916 of sequence 902'.

(e) symmetry/asymmetry: the difference between the numbers of frames associated with (a) the contraction closing and (b) the contraction opening of the contraction.

Other or different contraction data may be used, for example, the type of contraction (e.g., phasic or tonic; occlusive, non-occlusive, or semi-occlusive), the size or shape of the lumen opening or ranges thereof, the periodicity or frequency of opening and closing of the contractions, the degree of contractile occlusion, the presence of "wrinkles," or other color or pattern features or changes, etc.

The contraction data assigned to each captured sequences may be used, for example, to automatically characterize contractions and diagnose gastrointestinal motility disorders in the patient from which the images were captured. Contractile activity or sequences in an image stream may be tagged, flagged, marked, or otherwise indicated. For example, markers along a time bar or tissue color bar may visually indicate image frames associated with contractions. In another example, hidden or non-visual markers, such as flags in a data register or cache, or with metadata associated with frames, may indicate contractile frames or segments. In some embodiments, data processor 14 may automatically skip to the indicated contraction frames for processing and/or a monitor may automatically skip to display the indicated contraction frames. Other methods of identifying image frames depicting contractile activity may be used.

The contraction data may also be displayed, for example, in an integrated or adjacent display to the image stream display. Contraction data may be displayed as raw data or processed data, for example, including a quantitative analysis or automatic computer-recognized diagnosis. In one embodiment, the contraction data may be displayed in a map, table, profile, graph, or other data structure. For example, similar to a time bar, a contraction bar may indicate a contraction value corresponding to a frame or sequence being displayed. In one embodiment, the contraction bar may be a one-dimensional (1D) graph, including a line or bar increasing in length as the value of the corresponding contraction data increases. In one example, as the image stream is displayed, playing a sequence of frames over time, the contraction values displayed also change to match the contraction value for the current displayed frame. In another embodiment, the time and contraction values may be combined in a two-dimensional (2D) graph, for example, having an (x)-axis representing the playtime, such as a time bar, and a (y)-axis representing the contraction value(s) for the displayed frame. The 2D contraction graph may show the change in contraction data values, such as the size of the lumen opening in each frame, over the length of the entire moving image, the displayed portion, or for the template contraction sequence matching the current captured sequence being displayed. In one example, the 2D contraction graph, such as, a bar graph, may show values for a plurality of different contraction features, for example, the degree of phasic or tonic contraction in one bar, the degree of occlusion or non-occlusion in another bar, and the degree of symmetry/asymmetry in another bar. Thus, as the movie plays, the contraction bar(s) may show an instantaneous measure of the imaging device contraction features or an overall GI tract contraction data curve.

When the processor aligns frames for internal automatic sequence comparison, the modified frame alignment may or may not affect the display or viewing rate of captured frames. In one embodiment, the processor may display the frames in their original captured rate, for example, displaying each frame in a sequence with equal play-time. In another embodiment, the processor may display the frames in their modified rate, e.g., a standardized rate or a predetermined rate of the template contraction image stream. The modified rate may correspond to the elongated and/or compressed mapping, rate or length of the modified captured sequences. In another embodiment, the user may switch between displaying frames in the original captured rate (as possibly adjusted by standard display options such as pause or a user variable display rate) and the modified rate.

In some embodiments, metadata or other data associated or stored with frames in a sequence may indicate or store the re-alignment or other data associated with each frame or sequence (e.g., the size of the lumen opening, diagnoses, contraction data, and correspondences with template sequences). Changes to the metadata of a frame in one sequence may correspond to changes in the correspondence or alignment between the frames and other frames in another sequence. The metadata may be stored together with or separate from the frame data (e.g., in a storage unit 19 of FIG. 1).

Figure 10:
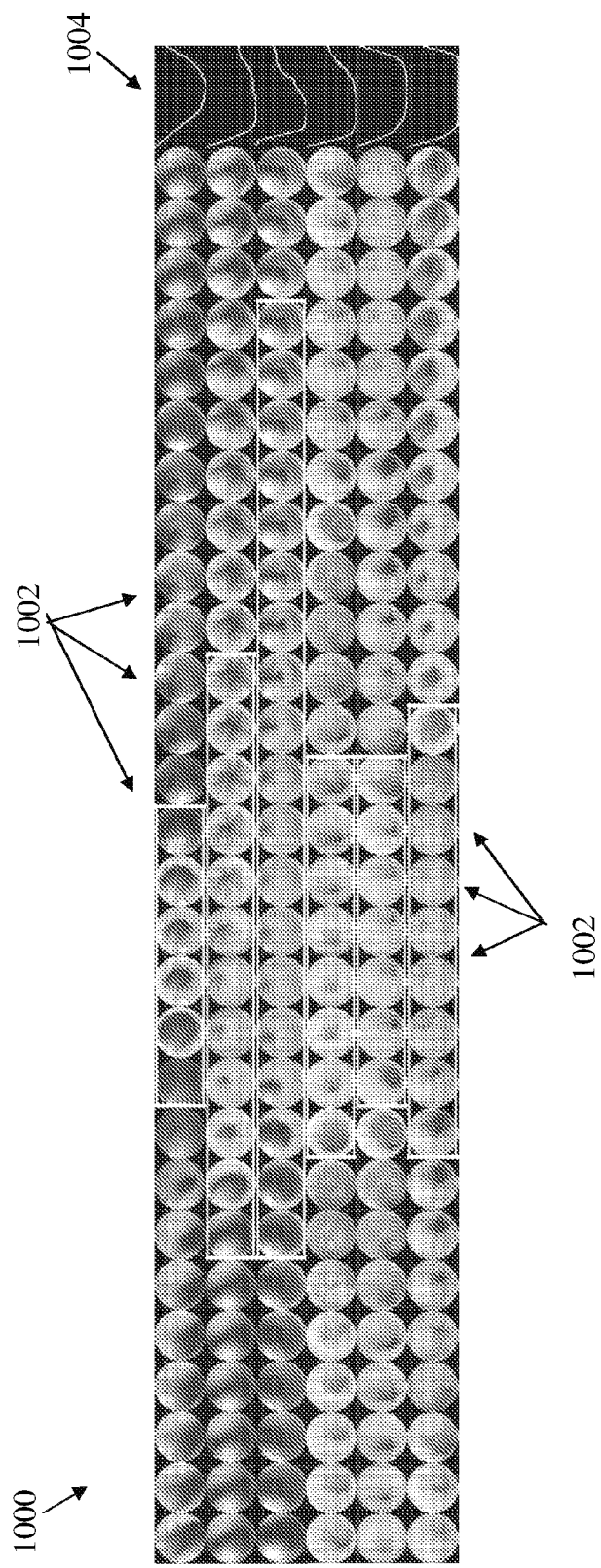
FIG. 10 is an example of a user display of detected contraction sequences, according to an embodiment of the present invention.

Reference is made to FIG. 10, which is an example of a user display of detected contraction sequences, according to an embodiment of the invention. A captured video stream may be displayed as one or more captured sequences 1000. The captured sequences 1000 may be displayed over time, in temporal succession, for example, as a moving image stream, or simultaneously in spatial succession, for example, as a film reel (e.g., as shown in FIG. 10). Captured sequences 1000 may or may not be filtered (e.g., by filter(s) 602 and/or 604 of FIG. 6).

Contraction sequences 1002 may be a sub-set of consecutive image frames in captured sequences 1000, which are identified as contraction frames (e.g., matching a template contraction sequence). In FIG. 10, contraction sequences 1002 may be marked by a surrounding white box or border. Other markers may be used.

Lumen size graph 1004 may display, for example, the lumen size or change in lumen size of each frame in captured sequences 1000 or only contraction sequences 1002. Lumen size graph 1004 may be normalized, for example, to values between zero (0) and one (1).

Figure 11A:
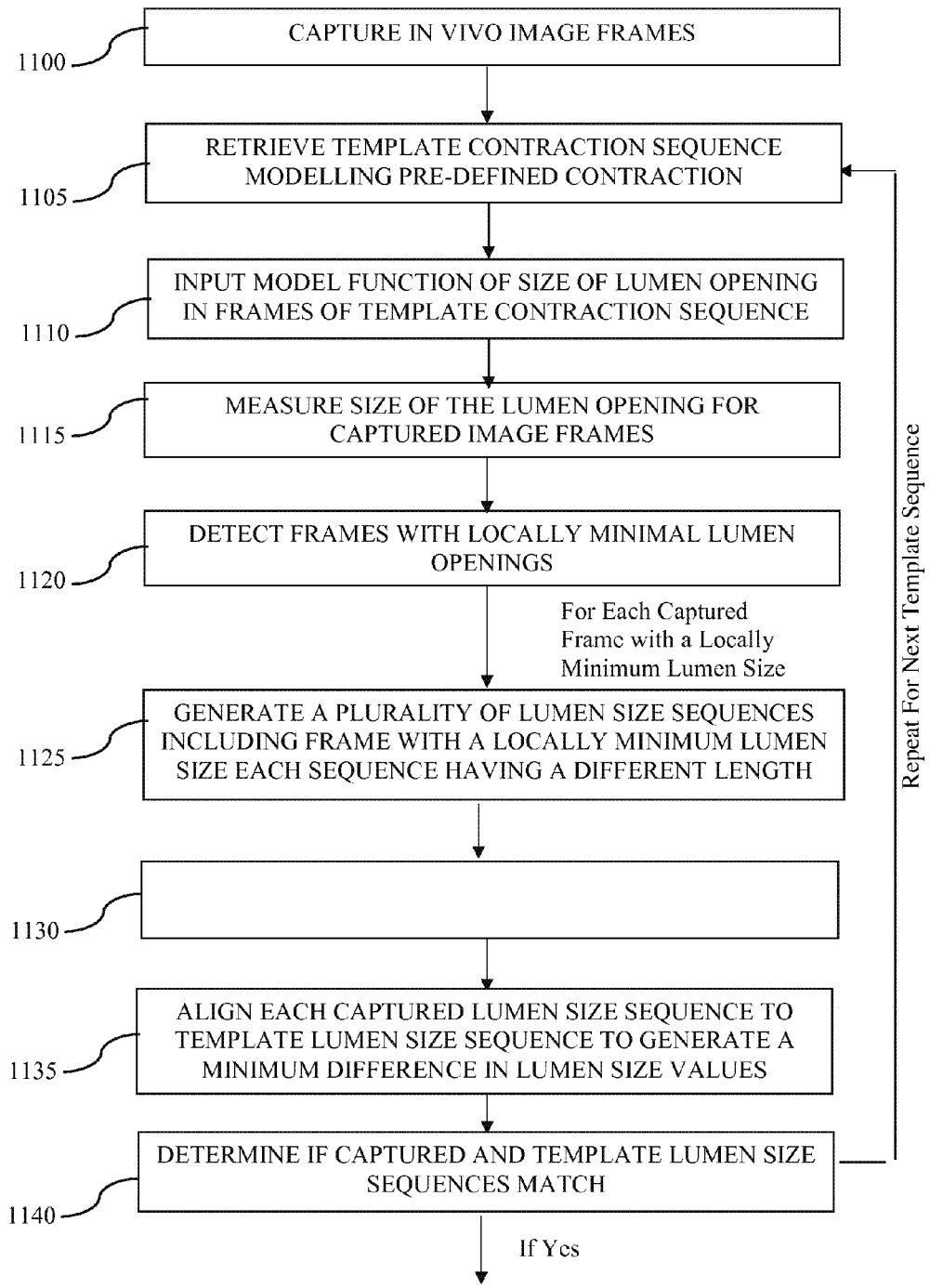
FIGS. 11A and 11B are flowcharts of a method, according to an embodiment of the invention.
Figure 11B:
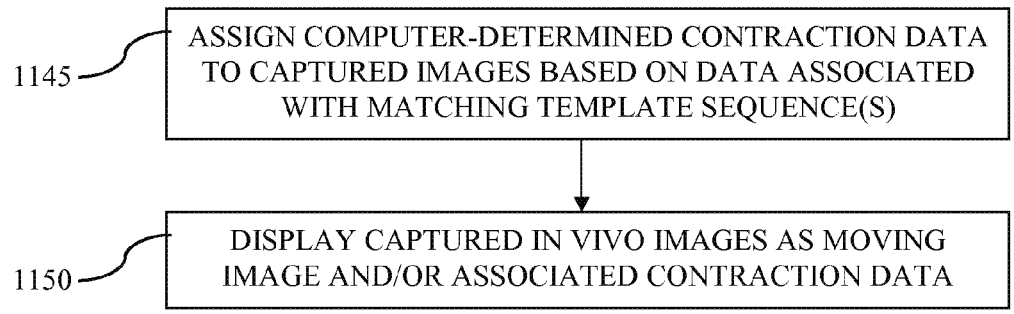

Reference is made to FIGS. 11A and 11B, which are flowcharts of a method for comparing sequences of in vivo images, according to an embodiment of the invention. Note that while the operations are described as being performed in sequence, they may be performed partially in parallel, or in a pipeline fashion.

In operation 1100, an autonomous imaging device (e.g., imaging device 40 of FIG. 1) may capture in vivo images while passively traversing the GI tract. The imaging device may include a transmitter, which may wirelessly transmits captured images while traversing the GI tract from inside a patient's body to a receiver disposed outside the patient's body. The captured images may be stored in a storage unit (e.g., storage unit 19 of FIG. 1) from which the processor may access the captured images.

In operation 1105, a processor (e.g., data processor 14 of FIG. 1) may retrieve a template contraction sequence, for example, from a plurality of template contraction sequences (e.g., template contraction sequences 200 of FIG. 2) stored in a memory unit (e.g., image database 10 of FIG. 1). Each of the plurality of template sequences may model a pre-defined contraction type and may be associated with different contraction data, annotations, or types of contractions.

The template contraction sequence may be automatically retrieved by the processor using criteria selected by a human operator or by an automatic retrieval process identifying the most relevant template sequences. For example, a processor may automatically determine and/or receive input from a user (e.g., via input device 24 of FIG. 1) indicating a target or possible diagnosis for a motility disorder (e.g., or more specifically for the presence of a certain disease, such as IBS-C). In this example, the processor may retrieve a template sequence associated with contraction characteristics related to the target diagnosis or disease.

In operation 1110, the processor may generate or receive a pre-generated model function or sequence, m, of the sizes of the lumen openings represented in each of the frames in the template contraction sequence. The processor may evaluate the lumen sizes of frames captured in operation 1100, for example, as a function of the number of pixels above a threshold grayscale value or the cumulative grayscale or color values of pixels. Since pixels inside the boundary of the lumen passageway are typically darker than other pixels, lumen opening pixels may be detected by detecting pixels having a greater than threshold level of darkness or black or a less than threshold level of brightness or red.

In operation 1115, the processor may measure the size of the lumen opening of an in-vivo lumen passageway represented in each of the captured image frames of an image stream captured in vivo to generate a lumen size function, $f$, of the captured image frames.

In operation 1120, the processor may detect or identify a subset of captured image frames, cf, having a local minimum size or smaller than threshold lumen passageway, which may be associated with the closing of the lumen wall at or near the center of some contractions (when symmetric and asymmetric, respectively).

A local minimum size lumen opening may be an exact or approximate size of a frame's lumen opening that is below a predetermined threshold minimum size, an exact or approximate smallest size lumen opening in a sequence of consecutive captured frames for example beginning and ending at frames having locally maximum lumen size openings, an exact or approximate smallest size lumen opening in a frame within a predetermined neighborhood or number of preceding and subsequent frames, an exact or approximate smallest size lumen opening in a frame of each sequence of equal or different lengths, a predetermined classifier value such as 0 or a negative value pre-associated with the local minimum size lumen opening, or any other sufficiently small values within a neighborhood or segment.

Similarly, a local maximum size lumen opening may be an exact or approximate size of a frame's lumen opening that is greater than a predetermined threshold maximum size, an exact or approximate greatest size lumen opening in a sequence of consecutive captured frames for example centered or including a frame having a local minimum lumen size openings, an exact or approximate greatest size lumen opening in a frame within a predetermined neighborhood or number of preceding and subsequent frames, an exact or approximate greatest size lumen opening in a frame of each sequence of equal or different lengths, a predetermined classifier value such as 1 or a positive value pre-associated with the local maximum size lumen opening, or any other sufficiently large values within a scene, sequence, neighborhood, or segment.

In operation 1125, for each frame, i in cf, with a local minimum sized lumen opening, the processor may generate a plurality of sequences, $s_i$, of the lumen sizes function, $f$, each sequence may have a different length. In one embodiment, each sequence, $s_i$, may be centered on or include the same minimum value lumen opening and each sequence may increase in the number of consecutive previous and subsequent frames extending outward from the minimum value. In one embodiment, the processor may divide the captured image stream at boundary frames having local maximum lumen sizes before and after the identified local minimum lumen sizes frame, i, to generate contraction sequences, $s_i$.

In operation 1130, the processor may scale each of the captured lumen size sequences, si, for example, to be the length of the template lumen size sequence, m.

In operation 1135, the processor may align the lumen size sequences, $s_i$ and m, for example, to generate a minimum cumulative difference between all correlated lumen size values. Multiple frames in one sequence may be correlated to a single frame in another. Typically the alignment preserves the order of the frames in each sequence, although in some embodiments, an alignment generating a different order may also be used.

In operation 1140, the processor may determine if the scaled and aligned lumen size sequences, $s_i$ and m, match or are sufficiently close, for example, by calculating an error or difference function therebetween.

If the sequences are not sufficiently close, no contraction is found in the associated frames, the process may return to operation 1105 and another template or model sequence may be retrieved and tested. However, if the sequences are sufficiently close, the associated frames of a captured sequence are identified to be a matching contraction and the process may proceed to operation 1145. The detected matching contraction frames or their metadata may be marked, flagged, or otherwise identified.

In one embodiment, the processor may first identify the lumen size sequences, $s_i$ that best fits or most closely matches the model sequence, m, for each frame i. If the cumulative difference between the lumen sizes for frames in the best fitting captured sequence and the model sequence are within a predetermined threshold range, the processor may determine that the best fitting captured sequence matches the model sequence and shows a contraction.

Operations 1120-1140 may be repeated for each frame, i, in set of minimum size lumen opening frames, cf, in the captured image stream.

In operation 1145, the processor may assign contraction data, for example, including a computer-determined diagnosis to the image stream including the captured in vivo images or a portion thereof (e.g., the captured sequence) based on an evaluation of the contraction data associated with captured image sequences in which matching contractions are detected (e.g., as described in reference to FIG. 9) or associated with the matching template sequence(s).

In operation 1150, a monitor (e.g., monitor 18 of FIG. 1) may display the matching contraction sequences, in spatial sequence as an array of frames or in temporal sequence as a moving image. The contraction sequences may be displayed separately from or together with the entire set of captured in vivo images (including non-contraction sequences). Alternatively, or additionally, the monitor may display the lumen size values or other contraction data associated with the frames of the contraction sequences, such as, the computer-determined diagnosis.

The monitor may display the captured in vivo images at a viewing rate proportional to the rate at which they were captured. Alternatively, the monitor may display the captured in vivo images at a standardized or rate or the scaled rate of the matching template sequence. In some embodiments, a user may enter a control command, which when received by the processor switches between the captured and scaled viewing rates. The viewing rate may or may not be adjusted based on the removal of filtered (e.g., turbid or static) frames. In some embodiments, contraction data and/or associated classifier values (e.g., assigned in FIG. 6) may be displayed as a map, table, or profile adjacent to the corresponding sequences through the image stream.

The processor may compare correlated frames associated with lumen sizes aligned in the lumen size sequences. When a one-to-many or many-to-one frame correlation is used, the processor may compare an associated multiple frames in one of the captured and template sequences with a single frame in the other of the captured and template sequences.

Other operations, orders of operations, and methods of comparing a captured image stream to template in-vivo sequences may be used. Various specific sets of methods may be combined in different embodiments and the method of FIGS. 11A and 11B may be executed alone or in combination with other processes described herein.

Manually entering visual annotation of contractions from an image stream captured by an imaging device may be laborious due to the typically large number of image frames (e.g., 50,000 frames) collected as it passes through the GI tract. Furthermore, visual analysis by a physician may depend on the particular viewing physician and may be non-standardized, for example, providing differences based on human variation, when compared to other patient records or a previous image stream taken of the same patient.

Accordingly, embodiments of the invention may generate an automated and standardized system to optimally analyze and annotate contractions in images of the GI tract.

Some embodiments of the invention may be utilized to selectively provide automatic or semi-automatic detection of in-vivo images (or frames of an in-vivo image stream), corresponding to contraction(s) and/or contractile activity. Some embodiments of the invention may allow a physician or operator to selectively view and/or rapidly access in-vivo images that correspond to contraction(s), and/or correspond to certain contractile activity (e.g., for diagnosis purposes, to locate or determine a dysfunction in contractile activity, or the like). Some embodiments of the invention may allow shortening of viewing time required by a physician for diagnosis, and/or shortening of time required by a physician to access and/or selectively view in-vivo images that correspond to contraction(s) and/or to contractile activity. Some embodiments of the invention may allow a selective display (or other presentation) of a portion (e.g., a relatively small portion, or multiple small portions) of an in-vivo image stream, which corresponds to contraction(s) and/or to contractile activity. Some embodiments of the invention may allow a physician to determine a portion-of-interest of an in-vivo image stream which the physician may examine, e.g., to detect a portion of an in-vivo image stream which corresponds to contraction(s) and/or contraction activity, for example, for further inspection by the physician. Some embodiments of the invention may allow to "skip" (e.g., by fast-forwarding) one or more portions of an in-vivo image stream based on contractile activity information, e.g., portion(s) that correspond to contractions and/or to contractile activity of interest, portion(s) that do not correspond to contractions and/or to contractile activity of interest, portions that correspond to existence of contractions and/or contractile activity, portions that correspond to absence of contractions and/or contractile activity, etc. Some embodiments of the invention may allow a physician to concentrate or "focus" his examination of an in-vivo image stream on a portion-of-interest, e.g., based on contraction(s) information and/or other contractile activity information that correspond to the portion-of-interest.

When used herein, a "score" or "rank" may be a general rating of a quality or evaluation. For example, in one embodiment the closer the scores between frames or sequences the greater the overall similarity therebetween, and (in another embodiment) a score may be associated with a specific property, e.g., a contraction type, a contraction symmetry score, a lumen size score, a score for the amount of change in lumen size between consecutive frames, a color score, a pathology score, a direction of image change, an amount of intestinal deformation between consecutive frames, or another score or measure that indicates a specific feature in the sequences. The individual scores of the frames may be combined as an average score measuring the similarity between the sequences. A similarity scores may represent, for example, a (normal or weighted) average of the difference in features between the captured and template sequences.

When used herein, a scene, sequence, or anatomical event may for example, include a plurality of frames depicting an in-vivo event such as a contraction (e.g., symmetric with equal duration of lumen opening and closing or asymmetric when opening and closing occurs at different speeds), a static sequence, a wrinkle sequence, or any other sequence. Each sequence may have the same or different length(s).

Although embodiments of the invention describe measuring, tracking and comparing the size of the lumen opening, for example, including pixels with an above threshold value on a gray scale, embodiments of the invention may equivalently measure, track and compare the size of the lumen wall (the structures not part of the lumen opening), for example, including pixels with a below threshold value on the gray scale.

Although embodiments of the invention describe assigning descriptor scores to each frame or frame pair, scores may similarly be assigned to each region of a frame, frame quadrant, individual pixel or pixel set, for example, of a 4×4 or 16×16 pixel block.

The frames may be analyzed for scoring, aligning, and matching, in a non-compressed form (analyzing absolute pixel values) and/or a compressed form (analyzing changes and relative pixel values). A compressed data header or other summary frame information package may indicate associated descriptor value(s). Compression mechanisms known in the art for expressing spatial changes within a frame or temporal changes between consecutive frames may be used.

It may be appreciated that although the frame analysis may be made after processing, frames may also be analyzed in "real-time" during frame capture and transmission.

It may be appreciated that an image or frame may be a digital or analog representation of real-life objects and that reference to objects in the frame may refer to the visual representation of those objects. For example, a lumen or characteristic of the lumen (such as lumen size or diameter) in an image may refer to a region of pixels in the image that visually represent a real-life lumen.

It is noted that while embodiments of the invention described herein are adapted for imaging of the GI tract, the devices and methods disclosed herein may be adapted for imaging other body cavities or spaces.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

Further embodiments are described in Appendix A attached hereto.

The invention claimed is:

1. A method, the method comprising:
measuring a size of an opening of an in-vivo lumen passageway represented in each frame in a subset of frames of an image stream captured in vivo;
identifying frames in the subset of frames of the image stream having a local minimum size of the lumen passageway;
dividing the subset of frames into segments of sequential frames at frames having local maximum lumen sizes before and after one or more of the identified frames having a local minimum size of the lumen passageway to generate contraction sequences; and
displaying a plurality of the contraction sequences.

2. The method of claim 1, wherein the captured image stream is divided into a plurality of captured sequences of different lengths.

3. The method of claim 1, comprising comparing the lumen sizes of the lumen passageway represented in frames of each captured contraction sequence with lumen sizes of the lumen passageway represented in correlated frames of a template contraction sequence.

4. The method of claim 3, comprising aligning a sequence of the lumen sizes of the lumen passageway represented in each captured contraction sequence with a sequence of the lumen sizes of the lumen passageway represented in the template contraction sequence to minimize cumulative differences in lumen sizes therebetween, and comparing correlated frames associated with lumen sizes aligned in the lumen size sequences.

5. The method of claim 4, comprising determining that the captured contraction sequence shows a contraction if the cumulative lumen size difference between the lumen passageways represented in aligned frames in the captured and template contraction sequences is within a predetermined threshold range.

6. The method of claim 3, comprising, scaling each different length lumen size sequence for captured contraction sequences to a single length of the lumen size sequence for the template contraction sequence.

7. The method of claim 3, wherein aligning comprises aligning lumen sizes of the lumen passageway represented in multiple frames in one lumen size sequence with lumen sizes of the lumen passageway represented in a single frame in another lumen size sequence and comparing the associated multiple frames in one of the captured and template sequences with a single frame in the other of the captured and template sequences.

8. The method of claim 1, comprising generating contraction data associated with the captured sequence determined to show a contraction, wherein the contraction data includes data selected from the group consisting of: the number of frames representing the closing of the contraction, the number of frames representing the opening of the contraction, the total number of frames representing the contraction, and the difference between the number of frames representing the closing and opening of the contraction.

9. A method, the method comprising:
receiving a sequence of sizes of lumen openings represented in each frame in a template image sequence of a contraction;
measuring a size of a lumen opening represented in each frame in a captured image stream;
identifying a plurality of frames within the captured image stream for which a local minimum lumen size is measured;
generating a plurality of captured sequences of different lengths from the captured image stream each captured sequence including at least one of the plurality of frames within the captured image stream for which a local minimum lumen size is measured;
identifying a best fitting one of the plurality of captured sequences having frames that most closely match the lumen sizes for the frames in the template image sequence; and
if a cumulative difference between the lumen sizes represented in frames in the best fitting captured sequence and the template image sequence are within a predetermined threshold range, determining that the captured sequence shows a contraction.

10. The method of claim 9 comprising comparing the lumen sizes of the lumen openings represented in frames of each captured sequence determined to show a contraction with lumen sizes of the lumen openings represented in correlated frames of the template image sequence of a contraction.

11. The method of claim 10 comprising aligning a sequence of the lumen sizes of the lumen openings represented in each captured sequence determined to show a contraction with a sequence of the lumen sizes of the lumen openings represented in the template image sequence to minimize cumulative differences in lumen sizes therebetween, and comparing correlated frames associated with lumen sizes aligned in the lumen size sequences.

12. A system comprising:
a processor to measure a size of an opening of an in-vivo lumen passageway represented in each frame in a subset of frames of an image stream captured in vivo, to identifying frames in the subset of frames of the image stream having a local minimum size of the lumen passageway, and to divide the subset of frames into segments of sequential frames at frames having local maximum lumen sizes before and after one or more of the identified frames having a local minimum size of the lumen passageway to generate contraction sequences; and
a display to display a plurality of the contraction sequences.

13. The system of claim 12, wherein the processor divides the captured image stream into a plurality of captured sequences of different lengths.

14. The system of claim 12, the processor compares the lumen sizes of the lumen passageway represented in frames of each captured contraction sequence with lumen sizes of the lumen passageway represented in correlated frames of a template contraction sequence.

15. The system of claim 14, wherein the processor aligns a sequence of the lumen sizes of the lumen passageway represented in each captured contraction sequence with a sequence of the lumen sizes of the lumen passageway represented in the template contraction sequence to minimize cumulative differences in lumen sizes therebetween, and compares correlated frames associated with lumen sizes aligned in the lumen size sequences.

16. The system of claim 14, wherein the processor determines that the captured contraction sequence shows a contraction if the cumulative lumen size difference between the lumen passageways represented in aligned frames in the captured and template contraction sequences is within a predetermined threshold range.

17. The system of claim 14, wherein the processor scales each different length lumen size sequence for captured contraction sequences to a single length of the lumen size sequence for the template contraction sequence.

18. The system of claim 14, wherein the processor aligns lumen sizes of the lumen passageway represented by multiple frames in one lumen size sequence with lumen sizes of the lumen passageway represented by a single frame in another lumen size sequence and compares the associated multiple frames in one of the captured and template sequences with a single frame in the other of the captured and template sequences.

19. The system of claim 12, wherein the processor generates contraction data associated with the captured sequence determined to show a contraction, wherein the contraction data includes data selected from the group consisting of: the number of frames representing the closing of the contraction, the number of frames representing the opening of the contraction, the total number of frames representing the contraction, and the difference between the number of frames representing the closing and opening of the contraction and the display displays the contraction data associated with the captured image stream.

* * * * *